(12) United States Patent
Bandman et al.

(10) Patent No.: US 6,399,345 B2
(45) Date of Patent: *Jun. 4, 2002

(54) SUBUNITS OF NADH DEHYDROGENASE

(75) Inventors: Olga Bandman, Mountain View; Surya K. Goli, Sunnyvale; Jennifer L. Hillman, San Jose, all of CA (US)

(73) Assignee: Incyte Genomics, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/151,412

(22) Filed: Sep. 10, 1998

Related U.S. Application Data

(62) Division of application No. 08/785,065, filed on Jan. 17, 1997, now Pat. No. 5,814,451.

(51) Int. Cl.[7] ............................. C12N 9/06; C12Q 1/26

(52) U.S. Cl. .......................................... 435/191; 435/25

(58) Field of Search .................... 435/191, 25; 424/94.4

(56) References Cited

FOREIGN PATENT DOCUMENTS

WO          94/03599          2/1994

OTHER PUBLICATIONS

Mariottini, P., et al. (1995) Met. Enzymol. 260, 202–210.*
Hofhaus, G, et al. (1995) Mol. Cell. Biol. 15(2), 964–974.*
Cleeter, M., et al., "The polypeptide composition of the mitochondrial NADH: ubiquinone reductase complex from several mammalian species," *Biochem. J.*, 230:739–746 (1985).
Walker, J., et al., "Sequences of 20 Subunits of NADH: Ubiquinone Oxidoreductase from Bovine Heart Mitochondria," *J. Mol. Biol.*, 226:1051–1072 (1992).
Pilkington, S., et al., "The 30–Kilodalton Subunit of Bovine Mitochondrial Complex I Is Homologous to a Protein Coded in Chloroplast DNA," *Biochem.*, 30:1901–1908 (1991).
Arizmendi, J., et al., "Complementary DNA sequences of two 14.5 kDa subunits of NADH:ubiquinone oxidoreductase from bovine heart mitochondria," *FEBS*, 313(1):80–84 (1992).
Iwahori, A., et al., Gcg Geneseq D Database entry Q57460, Accession No. Q57460, "NADH–ubiquinone oxido–reductase 30kDa subunit–like protein," XP002065894, Oct. 19, 1994.
Matsubara, K., et al., Gcg Geneseq D Database entry T19829, Accession No. T19829, "Human gene signature HUMGS00913," XP002065985, Jul. 12, 1996.

* cited by examiner

Primary Examiner—Charles L. Patterson, Jr.
(74) Attorney, Agent, or Firm—Incyte Genomics, Inc.

(57) ABSTRACT

The present invention provides four NADH dehydrogenase subunits (designated individually as NDS-1, NDS-2, NDS-3, and NDS-4 and collectively as NDS) and polynucleotides which identify and encode NDS. The invention also provides genetically engineered expression vectors and host cells comprising the nucleic acid sequences encoding NDS and a method for producing NDS. The invention also provides for use of NDS and agonists, antibodies, or antagonists specifically binding NDS, in the prevention and treatment of diseases associated with expression of NDS. Additionally, the invention provides for the use of antisense molecules to polynucleotides encoding NDS for the treatment of diseases associated with the expression of NDS. The invention also provides diagnostic assays which utilize the polynucleotide, or fragments or the complement thereof, and antibodies specifically binding NDS.

13 Claims, 17 Drawing Sheets

```
5' NGA ACT CTA ATA CGA GCA CTA TAG GGA AAG CTG GTA GCC TGC AGG TAC CGG TCC         54

GGA ATT CCC GGG TCG ACC CAC GCG TCC GCC GTG CCC TTG GGG CTC AGG CGT GTC CTG    108
    63                    72                   81                   90                   99

CTG TCT TTC CGT CCG CTG CCT AGT AAC ATG GCG GCG CTG GCG GCG GCG GCG GCG A      162
    117                  126                  135                  144                  153
                                                          M   A   A   L   A   A   A   A   A

GTA GCC AGG CTG TGG CGC GGG ATC TTG CCG GCC TCG GCC CTG GCG CTG ACC AGG GGG    216
    171                  180                  189                  198                  207
     V   A   R   L   W   R   G   I   L   P   A   S   A   L   A   L   T   R   G

ACT GGG CGA CCC TCC GTT CTG TTG CCG GTT AGG CGG GAG GCG CAC GCC GCC GGG GCC    270
    225                  234                  243                  252                  261
     T   G   R   P   S   V   L   L   P   V   R   R   E   A   H   A   A   G   A

GAC ACG CGC CCC ACT GTC AGA CCA CGG AAT GAT GTG GCC CAC AAG CAG CTC TCA        324
    279                  288                  297                  306                  315
     D   T   R   P   T   V   R   P   R   N   D   V   A   H   K   Q   L   S

GCT TTT GGA GAG TAT GTG GCT GAA ATC TTG CCC AAG TAT GTC CAA CAA GTT CAG        378
    333                  342                  351                  360                  369
     A   F   G   E   Y   V   A   E   I   L   P   K   Y   V   Q   Q   V   Q
```

FIGURE 1A

```
      387        396       405       414       423       432
GTG TCC TGC TTC AAT GAG TTA GAG GTC TGT ATC CAT CCT GAT GGC GTC ATC CCA
 V   S   C   F   N   E   L   E   V   C   I   H   P   D   G   V   I   P 441        450       459       468       477       486
GTG CTG ACT TTC CTC AGG GAT CAC ACC AAT GCA CAG TTC AAA TCT CTG GTT GAC
 V   L   T   F   L   R   D   H   T   N   A   Q   F   K   S   L   V   D 495        504       513       522       531       540
TTG ACA GCA GTG GAC GTC CCA ACT CGG CAA AAC CGT TTT GAG ATT GTC TAC AAC
 L   T   A   V   D   V   P   T   R   Q   N   R   F   E   I   V   Y   N 549        558       567       576       585       594
CTG TTG TCT CTG CGC TTC AAC TCA CGG ATC CGT GTG AAG ACC TAC ACA GAT GAG
 L   L   S   L   R   F   N   S   R   I   R   V   K   T   Y   T   D   E 603        612       621       630       639       648
CTG ACG CCC ATT GAG TCT GCT GTC TCT GTG TTC AAG GCA GCC AAC TGG TAT GAA
 L   T   P   I   E   S   A   V   S   V   F   K   A   A   N   W   Y   E 657        666       675       684       693       702
AGG GAG ATC TGG GAC ATG TTT GGA GTC TTC TTT GCT AAC CAC CCT GAT CTA AGA
 R   E   I   W   D   M   F   G   V   F   F   A   N   H   P   D   L   R 711        720       729       738       747       756
AGG ATC CTG ACA GAT TAT GGC TTC GAG GGA CAT CCT TTC CGG AAA GAC TTT CCT
 R   I   L   T   D   Y   G   F   E   G   H   P   F   R   K   D   F   P
```

FIGURE 1B

```
              765            774           783           792           801           810
     CTA TCT GGC TAT GTT GAG TTA CGT TAT GAT GAT GAA GTG AAG CGT GTG GTG GCA
      L   S   G   Y   V   E   L   R   Y   D   D   E   V   K   R   V   V   A 819            828           837           846           855           864
     GAG CCG GTG GAG TTG GCC CAA GAG TTC CGC AAA TTT GAC CTG AAC AGC CCC TGG
      E   P   V   E   L   A   Q   E   F   R   K   F   D   L   N   S   P   W 873            882           891           900           909           918
     GAG GCT TTC CCA GTC GAT TAT CGC CAA CCC GAG AGT CTC AAG CTT GAA GCC GGA
      E   A   F   P   V   D   Y   R   Q   P   E   S   L   K   L   E   A   G 927            936           945           954           963           972
     GAC AAG CCT GAT GCC AAG TAG CTC CAG GGA ACG CAT GTG GAT CCT AGA CAG
      D   K   P   D   A   K 981            990           999          1008          1017
     CGC CTT ATC TAT GAT TGA GTG TCC GTG TAA ATA AAT TCC TAC TTA GAC TTA C 3'
```

FIGURE 1C

```
5' NCC AAG ATG TCG TTC CCA AAG TAT AAG CCG TCG AGC CTG CGC ACT CTG CCT GAG   54
        M   S   F   P   K   Y   K   P   S   S   L   R   T   L   P   E

ACC CTC GAC CCA GCC GAA TAC AAC ATA TCT CCG GAA ACC CGG GCG CAA GCG           108
 T   L   D   P   A   E   Y   N   I   S   P   E   T   R   A   Q   A

GAG CGG TTG GCC ATA AGA GCC CAG CTG AAA CGA GAG TAC CTG CTT CAG TAC AAC      162
 E   R   L   A   I   R   A   Q   L   K   R   E   Y   L   L   Q   Y   N

GAT CCC AAC CGC CGA GGG CTC ATC GAA AAT CCT AAT TTC AGA GCC TTG CTT CGT TAT  216
 D   P   N   R   R   G   L   I   E   N   P   N   F   R   A   L   L   R   Y

GCA AGA ACA ATA AAT GTC TAT CCT AAT TTC AGA CCC ACT CCT AAA AAC TCA CTC      270
 A   R   T   I   N   V   Y   P   N   F   R   P   T   P   K   N   S   L

ATG GGA GCT CTG TGT GGA TTT GGG CCC CTC ATC TTC ATT TAT ATT ATC AAA          324
 M   G   A   L   C   G   F   G   P   L   I   F   I   Y   I   I   K

ACT GAG AGG GAT AGG AAA AAA GAA AAA CTT ATC CAG GAA GGA AAA TTG GAT CGA ACA  378
 T   E   R   D   R   K   K   E   K   L   I   Q   E   G   K   L   D   R   T
```

FIGURE 2A

```
     387       396       405       414       423       432
TTT CAC CTC TCA TAT TAA GTC TGG CAA TGA TGA CTA TAT GTA TTC CTG CCT AAA
 F   H   L   S   Y
    441       450
TAA ATC ATC TAT TAA TCA TT 3'
```

FIGURE 2B

```
5' NNA GCT AGT CGT TCT GAA GCG GCG GCC AGA GAA GAG TCA AGG GCA CGA GCA TCG   54

GCC ATG CCT TTC TTG GAC ATC CAG AGT GAA CAG TAC AAG AGG TTC GGC CTT AAC ATA GAT CGA TGG  108
        M   P   F   L   D   I   Q   S   E   Q   Y   K   R   F   G   L   N   I   D   R   W

TTG ACA ATC CAG AGT GAA GGT GAA CAG TAC CCC TAC AAG ATG GCT GGT CGA TGC CAT GCT  162
    L   T   I   Q   S   E   G   E   Q   P   Y   K   M   A   G   R   C   H   A

TTT GAA AAA GAA TGG ATA GAA TGT GCA CAT GGA ATC GGT TAT ACT CGG GCA GAG  216
    F   E   K   E   W   I   E   C   A   H   G   I   G   Y   T   R   A   E

AAA TGC AAG ATA GGT GCA ACC ATC AGG AAG CAG GAT TTC GTA GAG TGT TTG CTT CGG CAG AAA  270
    K   C   K   I   G   A   T   I   R   K   Q   D   F   V   E   C   L   L   R   Q   K

ACG ATG AGA CGT GCA GGT ACC ATC AGG AAG CAG CGG GAT AAG CTG ATA AAG GAA  324
    T   M   R   R   A   G   T   I   R   K   Q   R   D   K   L   I   K   E

GGA AAG TAC ACC CCT CCA CCT CAC CAC ATT GGC AAG GGG GAG CCT CGG CCC TGA  378
    G   K   Y   T   P   P   P   H   H   I   G   K   G   E   P   R   P   P
```

FIGURE 3A

```
     387           396           405           414           423           432
ACA GAG CAG CTG CTG ATG TCT GGA GGC TGA TTT TCC TGT TCT CTG TTC TCC ACT
     441           450           459           468
GGA AAG GTT GTT TAC GAC AAA CCT CCT TGT CAA AGT GTG T 3'
```

FIGURE 3B

```
                  9          18         27         36         45         54
5' CGC AGA GGA GGA GAA AGC TGA CCG CTT AGG CCC GGG TAG TGG TCG TCG TGG 63         72         81         90         99        108
   TTT TCC TTG TAG TTC GTG GTC TGA GAC CAG GCC TCA AGT GGA AAC GGC GTC ACC 117        126        135        144        153        162
   ATG ATC GCA CGG CGG AAC CCA GAA CCC TTA CGG TTT CTG CCG GAT GAG GCC CGG
    M   I   A   R   R   N   P   E   P   L   R   F   L   P   D   E   A   R 171        180        189        198        207        216
   AGC CTG TGC TCC GGC CCC CCG AAG CTG ACC GAC CCG CGG CTC CTC TAC ATC GGC TTC TTG
    S   L   C   S   G   P   P   K   L   T   D   P   R   L   L   Y   I   G   F   L 225        234        243        252        261        270
   GGC TAC TGC TCC GGC CTG ATT GAT AAC CTG ATC CGG CGG AGG CCG ATC GCG ACG
    G   Y   C   S   G   L   I   D   N   L   I   R   R   R   P   I   A   T 279        288        297        306        315        324
   GCT GGT TTG CAT CGC CAG NTT NTA TAT ATT ACG GCC TTT TTT GCT GGA TAT
    A   G   L   H   R   Q   X   X   Y   I   T   A   F   F   A   G   Y 333        342        351        360        369        378
   TAT NTT GTA AAA CGT GAA GAC TAC CTG TAT GCT GTG AGG GAC CGT GAA ATG TTT
    Y   X   V   K   R   E   D   Y   L   Y   A   V   R   D   R   E   M   F

FIGURE 4A
```

```
     387         396         405         414         423         432
GGA TAT ATG AAA TTA CAT CCA GAG GAT TTT CCT GAA GAT AAG AAA ACA TAT
 G   Y   M   K   L   H   P   E   D   F   P   E   D   K   K   T   Y 441         450         459         468         477         486
GGT GAA ATT TTT GAA AAA TTC CAT CCA ATA CGT TGA AGT CTT CAA AAT GCT TGC
 G   E   I   F   E   K   F   H   P   I   R 495         504         513         522         531         540
TCC AGT TTC ACT GAT ACC TGC TGT TTC TGA ATT TGA TGG AAC ATG TTT CTT ATG 549         558         567         576
ACA GTT GAA GCT TAT GCT AAT CTG TAT GTT GAC ACC  3'
```

FIGURE 4B

```
  1 M A A A A V A R L W - - W R G I L G A S A L T R G T G R P S V L L L P V R R E S   NDS-1
  1 M A A A V A A A P G C W Q R L V G S A A P A R V A G R P S V L L L P V R R E S     g163416

39 A G A D T R P T V R P R N D V A H K Q L S A F G E Y V A E I L P K Y V Q Q V Q V   NDS-1
 41 S A A D T R P T V R P R N D V A H K Q L S A F G E Y V A E I L P K Y V Q Q V Q V   g163416

79 S C F N E L E V C I H P D G V I P V L T F L R D H T N A Q F K S L V D L T A V D   NDS-1
 81 S C F N E L E I C I H P D G V I P V L T F L R D H S N A Q F K S L A D L T A V D   g163416

119 V P T R Q N R F E I V Y N L L S L R F N S R I R V K T Y T D E L T P I E S A V S   NDS-1
121 I P T R Q N R F E I V Y N L L S L R F N S R I R V K T Y T D E L T P I E S S V P   g163416

159 V F K A A N W Y E R E I W D M F G V F F A N H P D L R R I L T D Y G F E G H P F   NDS-1
161 V Y K A A N W Y E R E I W D M F G V F F A N H P D L R R I L T D Y G F E G H P F   g163416

199 R K D F P L S G Y V E L R Y D D E V K R V V A E P V E L A Q E F R K F D L N S P   NDS-1
201 R K D F P L S G Y V E L R Y D D E V K R V V A E P V E L A Q E F R K F D L N S P   g163416

239 W E A F P V Y R Q P P E S L K L E A G D K K P D A K                               NDS-1
241 W E A F P A Y R Q P P E S L K L E A G D T K P E A K                               g163416
```

FIGURE 5

```
  1 M S F P K Y K P S S L R T L P E T L D P A E Y N I S P E T R R A Q A E R L A I R   NDS-2
  1 M S F P K Y E A S R L S S L P T T L D P A E Y D I S S E T R K A Q A E R L A I R   gl14

41 A Q L K R E Y L L Q Y N D P N R R G L I E N P A L L R W A Y A R T I N V Y P N F   NDS-2
 41 S R L K R E Y Q L Q Y D P S R R G V I E D P A L V R W T Y A R S A N I Y P N F   gl14

81 R P T P K N S L M G A L C G F G P L I F Y Y I L K T E R D R K E K L I Q E G K   NDS-2
 81 R P N T K T S L L G A L F G I G P L V F W Y Y V V F K T D R D R K K E K L I E G K   gl14

121 L D R T F H L S Y   NDS-2
121 L D R T F N I S Y   gl14
```

FIGURE 6

```
 1  M P F L D I Q K R F G L N I D R W L T I Q S G E Q P Y K M A G R C H A F E K E W   NDS-3
 1  M P F F D V Q K R L G V D L D R W M T I Q S A E Q P H K K I P S R C H A F E K E W   g224

41  I E C A H G I G Y T R A E K E C K I E Y D D F V E C L L R Q K T M R R A G T I R   NDS-3
41  I E C A H G I G S I R A E K E C K I E F E D F R E C L L R Q K T M K R L H A I R   g224

81  K Q R D K L I K E G K Y T P P P H H I G K E P P R P                               NDS-3
81  R Q R E K L I K E G K Y T P P P H H H S G Q E E P R S                             g224
```

FIGURE 7

```
    1 MIA-RRNPEPLRFLPDEARSLPPPKLTDPRLLYIGFLGYC  NDS-4
    1 MMTGROGRATFQFLPDEARSLPPPKLTDPRLAFVGFLGYC  g582

40 SGLIDNLIRRRPIATAGLHRQXXYITAFFAGYYXVKRED   NDS-4
   41 SGLIDNAIRRRRPVLLAGLHRQLLYITSFVFVGYYLLKRQD g582

80 YLYAVRDREMFGYMKLHPEDFPEEDKKTYGEIFEKFHPIR  NDS-4
   81 YMYAVRDHDMFSYIKSHPEDFPEKDKKTYGEVFEEFHPVR  g582
```

FIGURE 8

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 264 amino acids
      (B) TYPE: amino acid
      (C) STRANDEDNESS: single
      (D) TOPOLOGY: linear (vii) IMMEDIATE SOURCE:
      (A) LIBRARY: Consensus
      (B) CLONE: Consensus (xi) SEQUENCE DESCRIPTION: SEQ ID NO:1:

```
Met Ala Ala Ala Val Ala Arg Leu Trp Trp Arg Gly Ile Leu Gly
 1               5                  10                  15

Ala Ser Ala Leu Thr Arg Gly Thr Gly Arg Pro Ser Val Leu Leu
                20                  25                  30

Pro Val Arg Arg Glu Ser Ala Gly Ala Asp Thr Arg Pro Thr Val Arg
                35                  40                  45

Pro Arg Asn Asp Val Ala His Lys Gln Leu Ser Ala Phe Gly Glu Tyr
     50                  55                  60

Val Ala Glu Ile Leu Pro Lys Tyr Val Gln Gln Val Gln Val Ser Cys
 65                  70                  75                  80

Phe Asn Glu Leu Glu Val Cys Ile His Pro Asp Gly Val Ile Pro Val
                85                  90                  95

Leu Thr Phe Leu Arg Asp His Thr Asn Ala Gln Phe Lys Ser Leu Val
                100                 105                 110

Asp Leu Thr Ala Val Asp Val Pro Thr Arg Gln Asn Arg Phe Glu Ile
                115                 120                 125

Val Tyr Asn Leu Leu Ser Leu Arg Phe Asn Ser Arg Ile Arg Val Lys
     130                 135                 140

Thr Tyr Thr Asp Glu Leu Thr Pro Ile Glu Ser Ala Val Ser Val Phe
145                 150                 155                 160

Lys Ala Ala Asn Trp Tyr Glu Arg Glu Ile Trp Asp Met Phe Gly Val
                165                 170                 175

Phe Phe Ala Asn His Pro Asp Leu Arg Arg Ile Leu Thr Asp Tyr Gly
                180                 185                 190

Phe Glu Gly His Pro Phe Arg Lys Asp Phe Pro Leu Ser Gly Tyr Val
                195                 200                 205

Glu Leu Arg Tyr Asp Asp Glu Val Lys Arg Val Val Ala Glu Pro Val
     210                 215                 220

Glu Leu Ala Gln Glu Phe Arg Lys Phe Asp Leu Asn Ser Pro Trp Glu
225                 230                 235                 240

Ala Phe Pro Val Tyr Arg Gln Pro Pro Glu Ser Leu Lys Leu Glu Ala
                245                 250                 255
```

Gly Asp Lys Lys Pro Asp Ala Lys
         260

(2) INFORMATION FOR SEQ ID NO:2:

(i) SEQUENCE CHARACTERISTICS:
        (A) LENGTH: 1023 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:2:

GAACTCTAAT ACGAGCACTA TAGGGAAAGC TGGTAGCCTG CAGGTACCGG TCCGGAATTC      60

CCGGGTCGAC CCACGCGTCC GCCGTGCCCT TGGGGCTCCG TGTCCTGCTG TCTTTCCGTC     120

CGCTGCCTAG TCTGCATCTG AGTAACATGG CGGCGGCGGC GGTAGCCAGG CTGTGGTGGC     180

GCGGGATCTT GGGGGCCTCG GCGCTGACCA GGGGGACTGG GCGACCCTCC GTTCTGTTGC     240

TGCCGGTGAG GCGGGAGAGC GCCGGGGCCG ACACGCGCCC CACTGTCAGA CCACGGAATG     300

ATGTGGCCCA CAAGCAGCTC TCAGCTTTTG GAGAGTATGT GGCTGAAATC TTGCCCAAGT     360

ATGTCCAACA AGTTCAGGTG TCCTGCTTCA ATGAGTTAGA GGTCTGTATC CATCCTGATG     420

GCGTCATCCC AGTGCTGACT TTCCTCAGGG ATCACACCAA TGCACAGTTC AAATCTCTGG     480

TTGACTTGAC AGCAGTGGAC GTCCCAACTC GGCAAAACCG TTTTGAGATT GTCTACAACC     540

TGTTGTCTCT GCGCTTCAAC TCACGGATCC GTGTGAAGAC CTACACAGAT GAGCTGACGC     600

CCATTGAGTC TGCTGTCTCT GTGTTCAAGG CAGCCAACTG GTATGAAAGG GAGATCTGGG     660

ACATGTTTGG AGTCTTCTTT GCTAACCACC CTGATCTAAG AAGGATCCTG ACAGATTATG     720

GCTTCGAGGG ACATCCTTTC CGGAAAGACT TTCCTCTATC TGGCTATGTT GAGTTACGTT     780

ATGATGATGA AGTGAAGCGT GTGGTGGCAG AGCCGGTGGA GTTGGCCCAA GAGTTCCGCA     840

AATTTGACCT GAACAGCCCC TGGGAGGCTT TCCCAGTCTA TCGCCAACCC CCGGAGAGTC     900

TCAAGCTTGA AGCCGGAGAC AAGAAGCCTG ATGCCAAGTA GCTCCAGGGA ACGCATGTGG     960

ATCCTAGACA GCGCCTTATC TATGATTGAG TGTCCGTGTA AATAAATTCC TACTTAGACT    1020

TAC                                                                 1023

(2) INFORMATION FOR SEQ ID NO:3:

(i) SEQUENCE CHARACTERISTICS:
        (A) LENGTH: 129 amino acids
        (B) TYPE: amino acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:3:

Met Ser Phe Pro Lys Tyr Lys Pro Ser Ser Leu Arg Thr Leu Pro Glu
  1               5                  10                  15

Thr Leu Asp Pro Ala Glu Tyr Asn Ile Ser Pro Glu Thr Arg Arg Ala
                 20                  25                  30

Gln Ala Glu Arg Leu Ala Ile Arg Ala Gln Leu Lys Arg Glu Tyr Leu
             35                  40                  45

```
Leu Gln Tyr Asn Asp Pro Asn Arg Arg Gly Leu Ile Glu Asn Pro Ala
        50                  55                  60

Leu Leu Arg Trp Ala Tyr Ala Arg Thr Ile Asn Val Tyr Pro Asn Phe
65                  70                  75                  80

Arg Pro Thr Pro Lys Asn Ser Leu Met Gly Ala Leu Cys Gly Phe Gly
                85                  90                  95

Pro Leu Ile Phe Ile Tyr Tyr Ile Ile Lys Thr Glu Arg Asp Arg Lys
            100                 105                 110

Glu Lys Leu Ile Gln Glu Gly Lys Leu Asp Arg Thr Phe His Leu Ser
        115                 120                 125

Tyr
```

(2) INFORMATION FOR SEQ ID NO:4:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:4:

```
CCAAGATGTC GTTCCCAAAG TATAAGCCGT CGAGCCTGCG CACTCTGCCT GAGACCCTCG    60

ACCCAGCCGA ATACAACATA TCTCCGGAAA CCCGGCGGGC GCAAGCGGAG CGGTTGGCCA   120

TAAGAGCCCA GCTGAAACGA GAGTACCTGC TTCAGTACAA CGATCCCAAC CGCCGAGGGC   180

TCATCGAAAA TCCTGCCTTG CTTCGTTGGG CCTATGCAAG AACAATAAAT GTCTATCCTA   240

ATTTCAGACC CACTCCTAAA AACTCACTCA TGGGAGCTCT GTGTGGATTT GGGCCCCTCA   300

TCTTCATTTA TTATATTATC AAAACTGAGA GGGATAGGAA AGAAAAACTT ATCCAGGAAG   360

GAAAATTGGA TCGAACATTT CACCTCTCAT ATTAAGTCTG GCAATGATGA CTATATGTAT   420

TCCTGCCTAA ATAAATCATC TATTAATCAT T                                  451
```

(2) INFORMATION FOR SEQ ID NO:5:

(i) SEQUENCE CHARACTERISTICS:
        (A) LENGTH: 106 amino acids
        (B) TYPE: amino acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:5:

```
Met Pro Phe Leu Asp Ile Gln Lys Arg Phe Gly Leu Asn Ile Asp Arg
1               5                   10                  15

Trp Leu Thr Ile Gln Ser Gly Glu Gln Pro Tyr Lys Met Ala Gly Arg
                20                  25                  30

Cys His Ala Phe Glu Lys Glu Trp Ile Glu Cys Ala His Gly Ile Gly
            35                  40                  45

Tyr Thr Arg Ala Glu Lys Glu Cys Lys Ile Glu Tyr Asp Asp Phe Val
        50                  55                  60

Glu Cys Leu Leu Arg Gln Lys Thr Met Arg Arg Ala Gly Thr Ile Arg
65                  70                  75                  80

Lys Gln Arg Asp Lys Leu Ile Lys Glu Gly Lys Tyr Thr Pro Pro Pro
```

85                  90                  95
His His Ile Gly Lys Gly Glu Pro Arg Pro
                100                 105

(2) INFORMATION FOR SEQ ID NO:6:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:6:

AGCTAGTCGT TCTGAAGCGG CGGCCAGAGA AGAGTCAAGG GCACGAGCAT CGGCCATGCC      60

TTTCTTGGAC ATCCAGAAAA GGTTCGGCCT TAACATAGAT CGATGGTTGA CAATCCAGAG     120

TGGTGAACAG CCCTACAAGA TGGCTGGTCG ATGCCATGCT TTTGAAAAAG AATGGATAGA     180

ATGTGCACAT GGAATCGGTT ATACTCGGGC AGAGAAAGAG TGCAAGATAG AATATGATGA     240

TTTCGTAGAG TGTTTGCTTC GGCAGAAAAC GATGAGACGT GCAGGTACCA TCAGGAAGCA     300

GCGGGATAAG CTGATAAAGG AAGGAAAGTA CACCCCTCCA CCTCACCACA TTGGCAAGGG     360

GGAGCCTCGG CCCTGAACAG AGCAGCTGCT GATGTCTGGA GGCTGATTTT CCTGTTCTCT     420

GTTCTCCACT GGAAAGGTTG TTTACGACAA ACCTCCTTGT CAAAGTGTGT                470

(2) INFORMATION FOR SEQ ID NO:7:

(i) SEQUENCE CHARACTERISTICS:
        (A) LENGTH: 119 amino acids
        (B) TYPE: amino acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:7:

Met Ile Ala Arg Arg Asn Pro Glu Pro Leu Arg Phe Leu Pro Asp Glu
  1               5                  10                  15

Ala Arg Ser Leu Pro Pro Pro Lys Leu Thr Asp Pro Arg Leu Leu Tyr
                 20                  25                  30

Ile Gly Phe Leu Gly Tyr Cys Ser Gly Leu Ile Asp Asn Leu Ile Arg
             35                  40                  45

Arg Arg Pro Ile Ala Thr Ala Gly Leu His Arg Gln Xaa Xaa Tyr Ile
 50                  55                  60

Thr Ala Phe Phe Phe Ala Gly Tyr Tyr Xaa Val Lys Arg Glu Asp Tyr
 65                  70                  75                  80

Leu Tyr Ala Val Arg Asp Arg Glu Met Phe Gly Tyr Met Lys Leu His
                 85                  90                  95

Pro Glu Asp Phe Pro Glu Glu Asp Lys Lys Thr Tyr Gly Glu Ile Phe
            100                 105                 110

Glu Lys Phe His Pro Ile Arg
        115

(2) INFORMATION FOR SEQ ID NO:8:

(i) SEQUENCE CHARACTERISTICS:

(A) LENGTH: 576 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: Consensus (xi) SEQUENCE DESCRIPTION: SEQ ID NO:8:

CGCAGAGGAG GAGGAGAAAG CTGACCGCTT AGGCCCGGGT AGTGGTCGTC GTGGTTTTCC      60

TTGTAGTTCG TGGTCTGAGA CCAGGCCTCA AGTGGAAACG GCGTCACCAT GATCGCACGG     120

CGGAACCCAG AACCCTTACG GTTTCTGCCG GATGAGGCCC GGAGCCTGCC CCCGCCCAAG     180

CTGACCGACC CGCGGCTCCT CTACATCGGC TTCTTGGGCT ACTGCTCCGG CCTGATTGAT     240

AACCTGATCC GGCGGAGGCC GATCGCGACG GCTGGTTTGC ATCGCCAGNT TNTATATATT     300

ACGGCCTTTT TTTTTGCTGG ATATTATNTT GTAAAACGTG AAGACTACCT GTATGCTGTG     360

AGGGACCGTG AAATGTTTGG ATATATGAAA TTACATCCAG AGGATTTTCC TGAAGAAGAT     420

AAGAAAACAT ATGGTGAAAT TTTTGAAAAA TTCCATCCAA TACGTTGAAG TCTTCAAAAT     480

GCTTGCTCCA GTTTCACTGA TACCTGCTGT TTCTGAATTT GATGGAACAT GTTTCTTATG     540

ACAGTTGAAG CTTATGCTAA TCTGTATGTT GACACC                              576

(2) INFORMATION FOR SEQ ID NO:9:

(i) SEQUENCE CHARACTERISTICS:
        (A) LENGTH: 266 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 163416

(xi) SEQUENCE DESCRIPTION: SEQ ID NO:9:

Met Ala Ala Val Ala Ala Ala Pro Gly Cys Trp Gln Arg Leu
 1               5                  10                  15

Val Gly Ser Ala Ala Pro Ala Arg Val Ala Gly Arg Pro Ser Val Leu
             20                  25                  30

Leu Leu Pro Val Arg Arg Glu Ser Ala Ala Asp Thr Arg Pro Thr
         35                  40                  45

Val Arg Pro Arg Asn Asp Val Ala His Lys Gln Leu Ser Ala Phe Gly
 50                  55                  60

Glu Tyr Val Ala Glu Ile Leu Pro Lys Tyr Val Gln Gln Val Gln Val
 65                  70                  75                  80

Ser Cys Phe Asn Glu Leu Glu Ile Cys Ile His Pro Asp Gly Val Ile
                 85                  90                  95

Pro Val Leu Thr Phe Leu Arg Asp His Ser Asn Ala Gln Phe Lys Ser
            100                 105                 110

Leu Ala Asp Leu Thr Ala Val Asp Ile Pro Thr Arg Gln Asn Arg Phe
        115                 120                 125

Glu Ile Val Tyr Asn Leu Leu Ser Leu Arg Phe Asn Ser Arg Ile Arg
    130                 135                 140

Val Lys Thr Tyr Thr Asp Glu Leu Thr Pro Ile Glu Ser Ser Val Pro
145                 150                 155                 160

Val Tyr Lys Ala Ala Asn Trp Tyr Arg Glu Ile Trp Asp Met Phe
                165                 170                 175

-continued

Gly Val Phe Ala Asn His Pro Asp Leu Arg Arg Ile Leu Thr Asp
            180                 185                 190

Tyr Gly Phe Glu Gly His Pro Phe Arg Lys Asp Phe Pro Leu Ser Gly
        195                 200                 205

Tyr Val Glu Leu Arg Tyr Asp Asp Glu Val Lys Arg Val Val Ala Glu
    210                 215                 220

Pro Val Glu Leu Ala Gln Glu Phe Arg Lys Phe Asp Leu Asn Ser Pro
225                 230                 235                 240

Trp Glu Ala Phe Pro Ala Tyr Arg Gln Pro Pro Glu Ser Leu Lys Leu
            245                 250                 255

Glu Ala Gly Asp Thr Lys Pro Glu Ala Lys
            260                 265

(2) INFORMATION FOR SEQ ID NO:10:

(i) SEQUENCE CHARACTERISTICS:
        (A) LENGTH: 129 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 114

(xi) SEQUENCE DESCRIPTION: SEQ ID NO:10:

Met Ser Phe Pro Lys Tyr Glu Ala Ser Arg Leu Ser Ser Leu Pro Thr
1               5                   10                  15

Thr Leu Asp Pro Ala Glu Tyr Asp Ile Ser Ser Glu Thr Arg Lys Ala
            20                  25                  30

Gln Ala Glu Arg Leu Ala Ile Arg Ser Arg Leu Lys Arg Glu Tyr Gln
        35                  40                  45

Leu Gln Tyr Tyr Asp Pro Ser Arg Arg Gly Val Ile Glu Asp Pro Ala
    50                  55                  60

Leu Val Arg Trp Thr Tyr Ala Arg Ser Ala Asn Ile Tyr Pro Asn Phe
65                  70                  75                  80

Arg Pro Asn Thr Lys Thr Ser Leu Leu Gly Ala Leu Phe Gly Ile Gly
            85                  90                  95

Pro Leu Val Phe Trp Tyr Tyr Val Phe Lys Thr Asp Arg Asp Arg Lys
            100                 105                 110

Glu Lys Leu Ile Gln Glu Gly Lys Leu Asp Arg Thr Phe Asn Ile Ser
        115                 120                 125

Tyr (2) INFORMATION FOR SEQ ID NO:11:

(i) SEQUENCE CHARACTERISTICS:
        (A) LENGTH: 106 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 224

(xi) SEQUENCE DESCRIPTION: SEQ ID NO:11:

Met Pro Phe Phe Asp Val Gln Lys Arg Leu Gly Val Asp Leu Asp Arg
1               5                   10                  15

Trp Met Thr Ile Gln Ser Ala Glu Gln Pro His Lys Ile Pro Ser Arg
            20                  25                  30

-continued

```
Cys His Ala Phe Glu Lys Glu Trp Ile Glu Cys Ala His Gly Ile Gly
        35                  40                  45

Ser Ile Arg Ala Glu Lys Glu Cys Lys Ile Glu Phe Glu Asp Phe Arg
        50                  55                  60

Glu Cys Leu Leu Arg Gln Lys Thr Met Lys Arg Leu His Ala Ile Arg
65                  70                  75                  80

Arg Gln Arg Glu Lys Leu Ile Lys Glu Gly Lys Tyr Thr Pro Pro Pro
                85                  90                  95

His His Ser Gly Gln Glu Glu Pro Arg Ser
                100                 105
```

(2) INFORMATION FOR SEQ ID NO:12:

(i) SEQUENCE CHARACTERISTICS:
        (A) LENGTH: 120 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 582

(xi) SEQUENCE DESCRIPTION: SEQ ID NO:12:

```
Met Met Thr Gly Arg Gln Gly Arg Ala Thr Phe Gln Phe Leu Pro Asp
1               5                   10                  15

Glu Ala Arg Ser Leu Pro Pro Pro Lys Leu Thr Asp Pro Arg Leu Ala
                20                  25                  30

Phe Val Gly Phe Leu Gly Tyr Cys Ser Gly Leu Ile Asp Asn Ala Ile
            35                  40                  45

Arg Arg Arg Pro Val Leu Leu Ala Gly Leu His Arg Gln Leu Leu Tyr
        50                  55                  60

Ile Thr Ser Phe Val Phe Val Gly Tyr Tyr Leu Leu Lys Arg Gln Asp
65                  70                  75                  80

Tyr Met Tyr Ala Val Arg Asp His Asp Met Phe Ser Tyr Ile Lys Ser
                85                  90                  95

His Pro Glu Asp Phe Pro Glu Lys Asp Lys Lys Thr Tyr Gly Glu Val
                100                 105                 110

Phe Glu Glu Phe His Pro Val Arg
            115                 120
```

SUBUNITS OF NADH DEHYDROGENASE

This application is a divisional application of U.S. application Ser. No. 08/785,065, filed Jan. 17, 1997 now U.S. Pat. No. 5,814,451.

FIELD OF THE INVENTION

This invention relates to nucleic acid and amino acid sequences of polypeptide subunits of NADH dehydrogenase and to the use of these sequences in the diagnosis, prevention, and treatment of cancer, myopathies, neurodegenerative diseases, immune system disorders, and diseases and disorders of the sympathetic nervous system.

BACKGROUND OF THE INVENTION

NADH dehydrogenase (NADH:ubiquinone oxidoreductase, NADH-D) is the first multienzyme complex (Complex I) in a chain of three complexes that make up the mitochondrial electron transport chain. The mitochondrial electron transport chain is responsible for the transport of electrons from NADH to oxygen and the coupling of this oxidation to the synthesis of ATP (oxidative phosphorylation) which provides the energy source for driving a cell's many energy-requiring reactions. NADH-D accomplishes the first step in this process by accepting electrons from NADH and passing them through a flavin molecule to ubiquinone, which transfers the electrons to the second enzyme complex in the chain.

NADH-D and the other members of the electron transport chain are located in the mitochondrial membrane. NADH-D is the largest of the three complexes with an estimated mass of 800 kDa comprising some 40 polypeptides of widely varying size and composition. The polypeptide composition of NADH-D in a variety of mammalian species including rat, rabbit, cow, and man is very similar (Cleeter, M. W. J. and Ragan, C. I. (1985) Biochem. J. 230: 739–46). The best characterized NADH-D is from bovine heart mitochondria and is composed of 41 polypeptide chains (Walker, J. E. et al. (1992) J. Mol. Biol. 226: 1051–72). Seven of these polypeptides are encoded by mitochondrial DNA while the remaining 34 are nuclear gene products that are imported into the mitochondria. These imported polypeptides are characterized by various N-terminal peptide sequences or modified N-terminal amino acids (myristoylation or acetylation) that target them to the mitochondria and are then cleaved from the mature protein. The 24-, 51-, and 75-kDa subunits have been identified as being catalytically important in electron transport, with the 51-kDa subunit forming part of the NADH binding site and containing the flavin moiety that is the initial electron acceptor. The location of other functionally important groups, such as the electron-carrying iron sulfate centers, remains to be determined. Many of the smaller subunits (<30 kDa) may play a purely structural role in the complex.

Defects and altered expression of NADH-D are associated with a variety of disease conditions in man, incluing; neurodegenerative diseases, myopathies, and cancer. In addition, NADH-D reduction of the quinone moiety in chemotherapeutic agents such as doxorubicin is believed to contribute to the antitumor activity and/or mutagenicity of these drugs.

The discovery of polynucleotides encoding NADH dehydrogenase, and the molecules themselves, provides a means to investigate the control of cellular respiration under normal and disease conditions. Such molecules related to NADH dehydrogenase satisfy a need in the art by providing new diagnostic or therapeutic compositions useful in diagnosing and treating cancers, myopathies, neurodegenerative diseases, and diseases and disorders of the sympathetic nervous system.

SUMMARY OF THE INVENTION

The present invention features four NADH dehydrogenase subunits, designated individually as NDS-1, NDS-2, NDS-3 and NDS-4 and collectively as NDS, and characterized as having similarity to NADH dehydrogenase.

Accordingly, the invention features substantially purified NDS proteins NDS-1, NDS-2, NDS-3, and NDS-4 having the amino acid sequences shown in SEQ ID NO:1, SEQ ID NO:3, SEQ ID NO:5 and SEQ ID NO:7, respectively.

One aspect of the invention features isolated and substantially purified polynucleotides that encode NDS proteins. In a particular aspect, the polynucleotides are the nucleotide sequences of SEQ ID NO:2, SEQ ID NO:4, SEQ ID NO:6, or SEQ ID NO:8 respectively.

The invention also features a polynucleotide sequence comprising the complement of SEQ ID NO:2, SEQ ID NO:4, SEQ ID NO:6, SEQ ID NO:8 or variants thereof. In addition, the invention features polynucleotide sequences which hybridize under stringent conditions to SEQ ID NO:2, SEQ ID NO:4, SEQ ID NO:6, or SEQ ID NO:8.

The invention additionally features nucleic acid sequences encoding polypeptides, oligonucleotides, peptide nucleic acids (PNA), fragments, portions or antisense molecules thereof, and expression vectors and host cells comprising polynucleotides that encode NDS. The present invention also features antibodies which bind specifically to NDS, and pharmaceutical compositions comprising substantially purified NDS. The invention also features the use of agonists and antagonists of NDS.

BRIEF DESCRIPTION OF THE FIGURES

FIGS. 1A, 1B, and 1C show the amino acid sequence (SEQ ID NO:1 and nucleic acid sequence (SEQ ID NO:2) of NDS-1. The alignment was produced using MacDNASIS PRO software (Hitachi Software Engineering Co., Ltd., San Bruno, Calif.).

FIGS. 2A and 2B show the amino acid sequence (SEQ ID NO:3) and nucleic acid sequence (SEQ ID NO:4) of NDS-2.

FIGS. 3A and 3B show the amino acid sequence (SEQ ID NO:5) and nucleic acid sequence (SEQ ID NO:6) of NDS-3.

FIGS. 4A and 4B show the amino acid sequence (SEQ ID NO:7) and nucleic acid sequence (SEQ ID NO:8) of NDS-4.

FIG. 5 shows the amino acid sequence alignments between NDS-1 (SEQ ID NO:1) and the bovine heart 30-kDa subunit (GI 163416; SEQ ID NO:9). The alignment was produced using the multisequence alignment program of (DNASTAR Inc., Madison, Wis.).

FIG. 6 shows the amino acid sequence alignments between NDS-2 (SEQ ID NO:3) and the bovine heart B 15 subunit (GI 114; SEQ ID NO:10).

FIG. 7 shows the amino acid sequence alignments between NDS-3 (SEQ ID NO:5) and the bovine heart 15-kDa (IP) subunit (GI 224; SEQ ID NO:11).

FIG. 8 shows the amino acid sequence alignments between NDS-4 (SEQ ID NO:7) and the bovine heart B14.5b subunit (GI 582; SEQ ID NO:12).

DESCRIPTION OF THE INVENTION

Figure 9A:
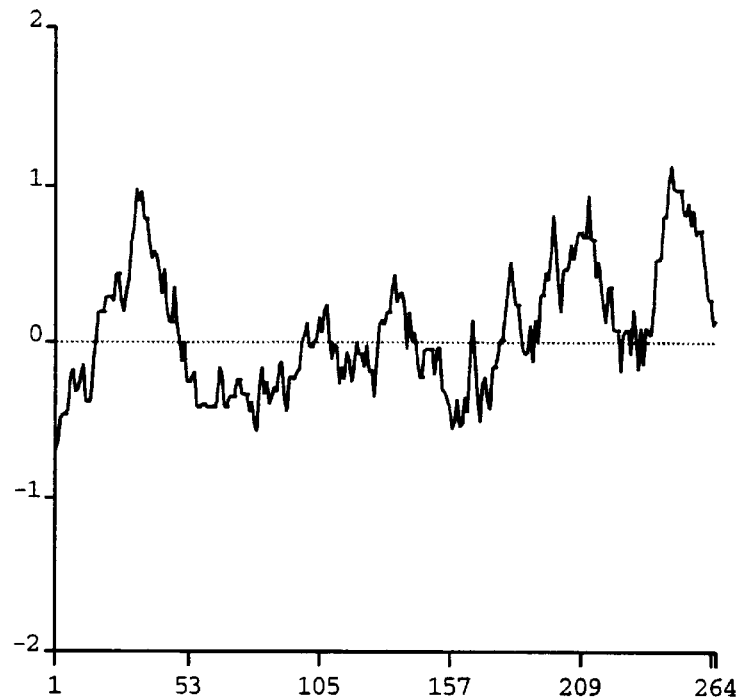
FIGS. 9A and 9B show the hydrophobicity plots (MACDNASIS PRO software) for NDS-1, (SEQ ID NO:1) and bovine heart 30-kDa subunit (SEQ ID NO:9). The positive X axis reflects amino acid position, and the negative Y axis reflects hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence", as used herein, refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

NDS, as used herein, refers to the amino acid sequences of substantially purified NDS obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of NDS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic NDS, or any oligopeptide thereof, to induce a specific immune response in appropriate animals or cells and to bind with specific antibodies.

The term "agonist", as used herein, refers to a molecule which, when bound to NDS, causes a change in NDS which modulates the activity of NDS. Agonists may include proteins, nucleic acids, carbohydrates, or any other molecules which bind to NDS.

The terms "antagonist" or "inhibitor", as used herein, refer to a molecule which, when bound to NDS, blocks or modulates the biological or immunological activity of NDS. Antagonists and inhibitors may include proteins, nucleic acids, carbohydrates, or any other molecules which bind to NDS.

The term "modulate", as used herein, refers to a change or an alteration in the biological activity of NDS. Modulation may be an increase or a decrease in protein activity, a change in binding characteristics, or any other change in the biological, functional or immunological properties of NDS.

The term "mimetic", as used herein, refers to a molecule, the structure of which is developed from knowledge of the structure of NDS or portions thereof and, as such, is able to effect some or all of the actions of NADH-D protein-like molecules.

The term "derivative", as used herein, refers to the chemical modification of a nucleic acid encoding NDS or the encoded NDS. Illustrative of such modifications would be replacement of hydrogen by an alkyl, acyl, or amino group.

A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be firther stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by basepairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human NDS and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding NDS or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2, SEQ ID NO:4, SEQ ID NO:6, or SEQ ID NO:8 by northern analysis is indicative of the presence of mRNA encoding NDS in a sample and thereby correlates with expression of the transcript from the polynucleotide encoding the protein.

"Alterations" in the polynucleotide of SEQ ID NO:2, SEQ ID NO:4, SEQ ID NO:6, or SEQ ID NO:8 as used herein, comprise any alteration in the sequence of polynucleotides encoding NDS including deletions, insertions, and point mutations that may be detected using hybridization assays. Included within this definition is the detection of alterations to the genomic DNA sequence which encodes NDS (e.g., by alterations in the pattern of restriction fragment length polymorphisms capable of hybridizing to SEQ ID NO:2, SEQ ID NO:4, SEQ ID NO:6, or SEQ ID NO:8), the inability of a selected fragment of SEQ ID NO:2, SEQ ID NO:4, SEQ ID NO:6, or SEQ ID NO:8 to hybridize to a sample of genomic DNA (e.g., using allele-specific oligonucleotide probes), and improper or unexpected hybridization, such as hybridization to a locus other than the normal chromosomal locus for the polynucleotide sequence encoding NDS (e.g., using fluorescent in situ hybridization (FISH) to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind NDS polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of NADH dehydrogenase subunits (NDS-1, NDS-2, NDS-3, and NDS-4, collectively referred to as NDS), the polynucleotides encoding NDS, and the use of these compositions for the diagnosis, prevention, or treatment of cancers, myopathies, neurodegenerative diseases, and diseases and disorders of the sympathetic nervous system.

Nucleic acid sequences encoding the human NDS-1 of the present invention were first identified in Incyte Clone 4401 from a human mast cell line, HMC-1cDNA library (HMC1NOT01) through a computer-generated search for amino acid sequence alignments. A consensus sequence, SEQ ID NO:2, was derived from this same clone.

Nucleic acid sequences encoding the human NDS-2 of the present invention were first identified in Incyte Clone 1600202 from a bladder tissue cDNA library (BLADNOT03) through a computer-generated search for amino acid sequence alignments. A consensus sequence, SEQ ID NO:4, was derived from the following overlapping and/or extended nucleic acid sequences (cDNA library from which derived): Incyte Clones 571087 (MMLR3DT01); 966781 (BRSTNOT05); 1600202 (BLADNOT03); and 1913211 (PROSTUT04).

Nucleic acid sequences encoding the human NDS-3 of the present invention were first identified in Incyte Clone 1708121, from a prostate tissue cDNA library (PROSNOT16) through a computer-generated search for amino acid sequence alignments. A consensus sequence, SEQ ID NO:6, was derived from the following overlapping and/or extended nucleic acid sequences (cDNA library from which derived): Incyte Clones 928553 (BRAINOT04); 957042 (KIDNNOT05); and 1708121 (PROSNOT16).

Nucleic acid sequences encoding the human NDS-4 of the present invention were first identified in Incyte Clone 1996788, from a breast tumor tissue cDNA library (BRSTTUT03) through a computer-generated search for amino acid sequence alignments. A consensus sequence, SEQ ID NO:6, was derived from the following overlapping and/or extended nucleic acid sequences (cDNA library from which derived): Incyte Clones 623462 (PGANNOT01); 835412 (PROSNOT07); 1381432 (BRAITUT08); and 1996788 (BRSTTUT03).

Figure 9B:
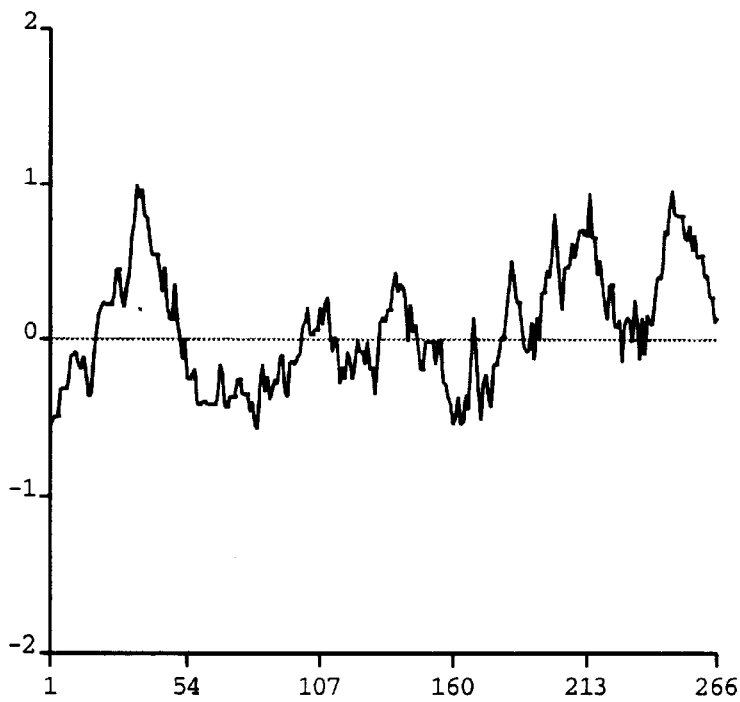

In one embodiment, the invention encompasses a polypeptide comprising the amino acid sequence of SEQ ID NO:1, and shown in FIGS. 1A, 1B, and 1C. As shown in FIG. 5, NDS-1 has chemical and structural homology with bovine 30-kDa subunit (GI 163416). In particular, NDS-1 shares 90% overall identity with bovine 30-kDa subunit. An N-terminal signal sequence in the bovine 30-kDa subunit that extends from residues M1 to R37 and serves to direct the protein to the mitochondria is well conserved in NDS-1. The sequence is cleaved in the mature protein following the translocation process. In particular, a high content of arginine and alanine that is characteristic of these signal sequences is apparent in both proteins, as is the presence of an arginine at position −2 relative to the cleavage point at E37. Within the sequence of the mature protein, beginning at residue E37, the identity between NDS-1 and the bovine 30-kDa subunit is 95%. As illustrated by FIGS. 9A and 9B, NDS-1 and the bovine 30-kDa subunit have similar hydrophobicity plots. Northern analysis indicates that transcripts of the gene encoding NDS-1 are most abundant in cDNA libraries from cancerous tissues and immortalized cell lines (21/64), in tissues associated with the immune system (12/64), in smooth muscle tissues (14/64) and in brain tissue (9/64).

Figure 10A:
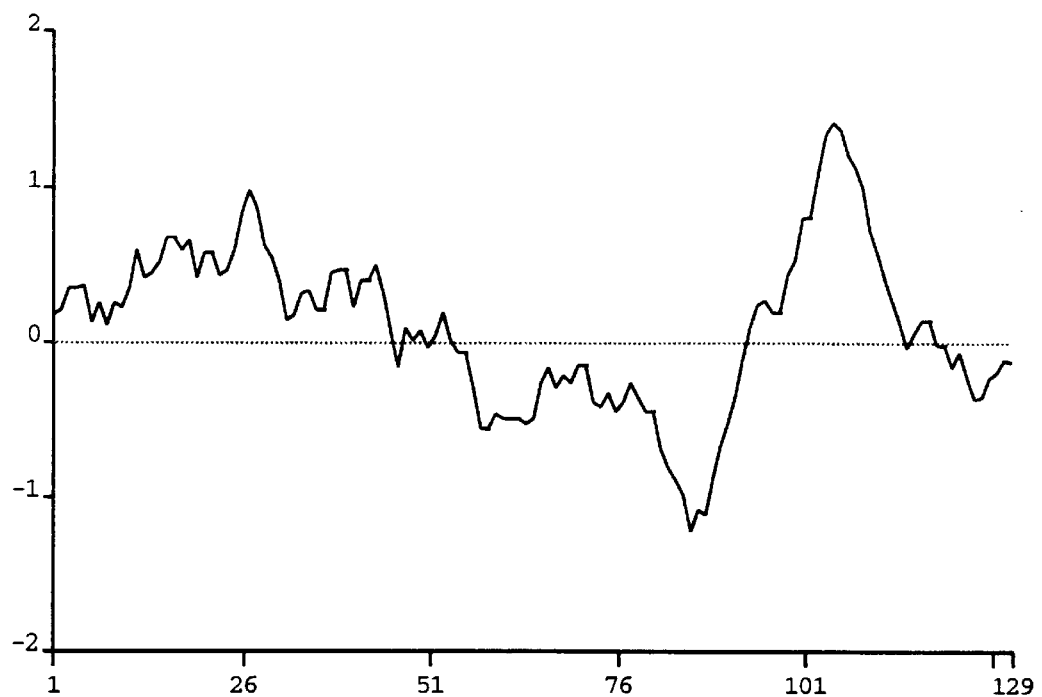
FIGS. 10A and 10B show the hydrophobicity plots for NDS-2, (SEQ ID NO:3) and bovine heart B15 subunit, (SEQ ID NO:10).
Figure 10B:
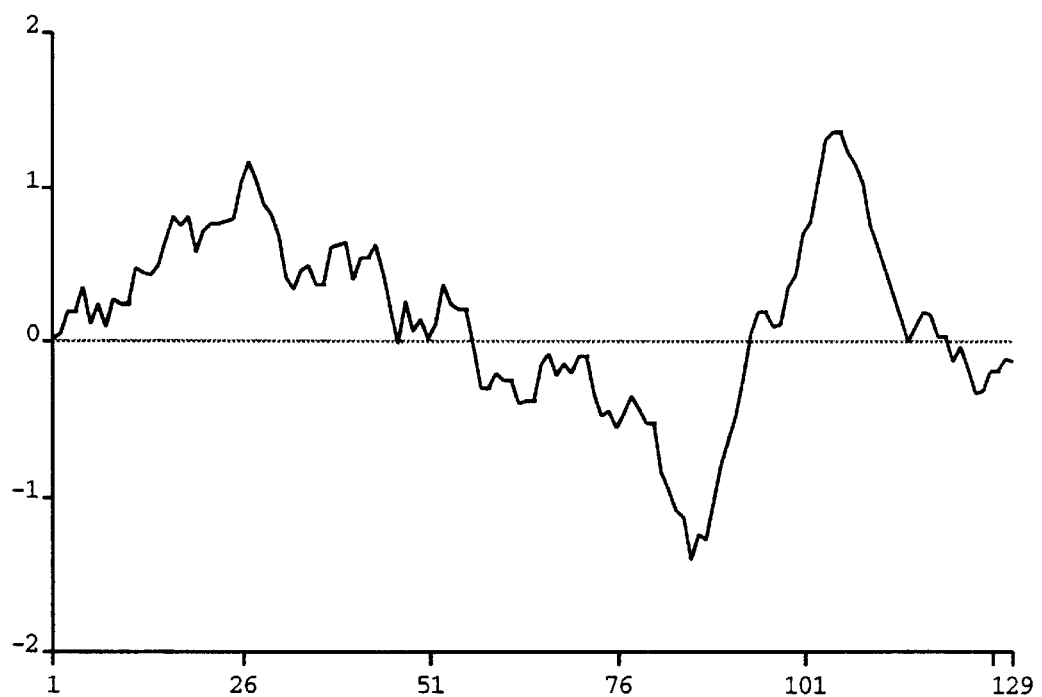

In another embodiment, the invention encompasses a polypeptide comprising the amino acid sequence of SEQ ID NO:3, as shown in FIGS. 2A and 2B. NDS-2 is 129 amino acids in length. As shown in FIG. 6, NDS-2 has chemical and structural homology with the bovine B15 subunit (GI 114). In particular, NDS-2 and 15-kDa (IP) share 74% identity. B15 is one of several nuclear encoded NADH-D subunits that lacks an N-terminal signal sequence, but is N-acetylated at an adjacent alanine or serine residue following removal of the initiator methionine. Both NDS-2 and B 15 share the critical serine residue in position 2. As illustrated by FIGS. 10A and 10B, NDS-2 and B15 have rather similar hydrophobicity plots. In particular NDS-2 and B15 share a peak of hydrophobicity between approximately residues 90 to 115 that is believed to be a membrane spanning alpha-helix. Northern analysis indicates that partial transcripts of the gene encoding NDS-1 are most abundant in cDNA libraries from cancerous tissues (26/81), particularly in prostate, brain, and bladder tumors, and in smooth muscle tissues (26/81). It is also notable in fetal and neonatal tissues, the brain and spinal cord, and in cells of the immune system.

Figure 11A:
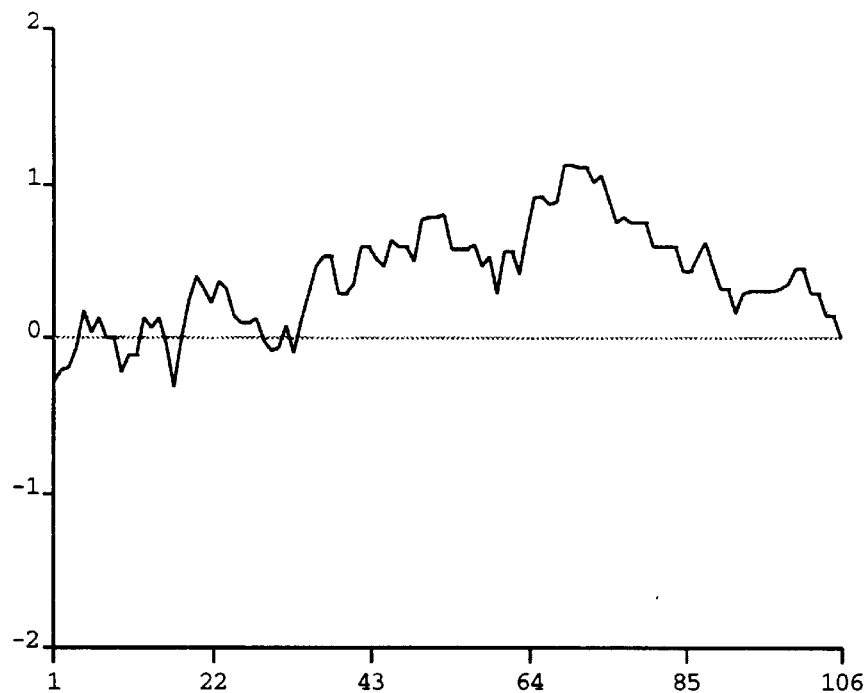
FIGS. 11A and 11B show the hydrophobicity plots for NDS-3, (SEQ ID NO:5) and bovine heart 15-kDa (IP) subunit, (SEQ ID NO:11).
Figure 11B:
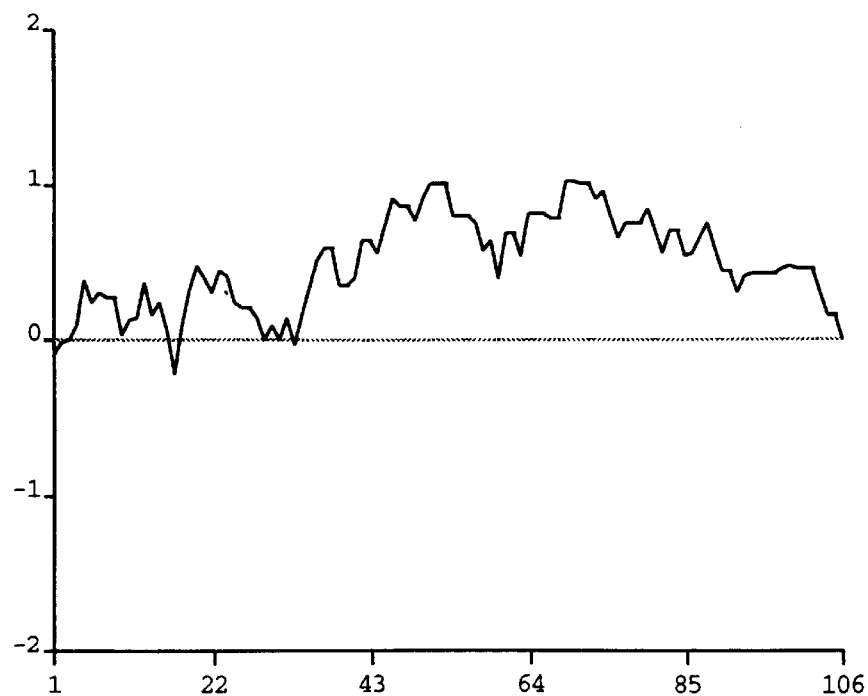

In another embodiment, the invention encompasses a polypeptide comprising the amino acid sequence of SEQ ID NO:5, as shown in FIGS. 3A and 3B NDS-3 is 106 amino acids in length. As shown in FIG. 7, NDS-3 has chemical and structural homology with the bovine 15-kDa (IP) subunit (GI 224). In particular, NDS-3 and 15-kDa (IP) share 75% identity. The 15-kDa subunit is one of several subunits found in the iron-suifir protein (IP) fraction during purification of NADH-D. The 15-kDa subunit contains four cysteine residues, all of which are shared by NDS-3, that may form one of the iron-sulfur centers that functions in electron transport. As illustrated by FIGS. 11A and 11B, NDS-3 and 15-kDa (IP) have rather similar hydrophobicity plots. Northern analysis indicates that partial transcripts of the gene encoding NDS-3 are most abundant in cDNA libraries from cancerous tissues and immortalized cell lines (28/88), smooth muscle tissues (17/88), and in brain and neural tissues (10/88). They are also found in fetal, developing tissues and in tissues associated with inflammation and the immune response.

Figure 12A:
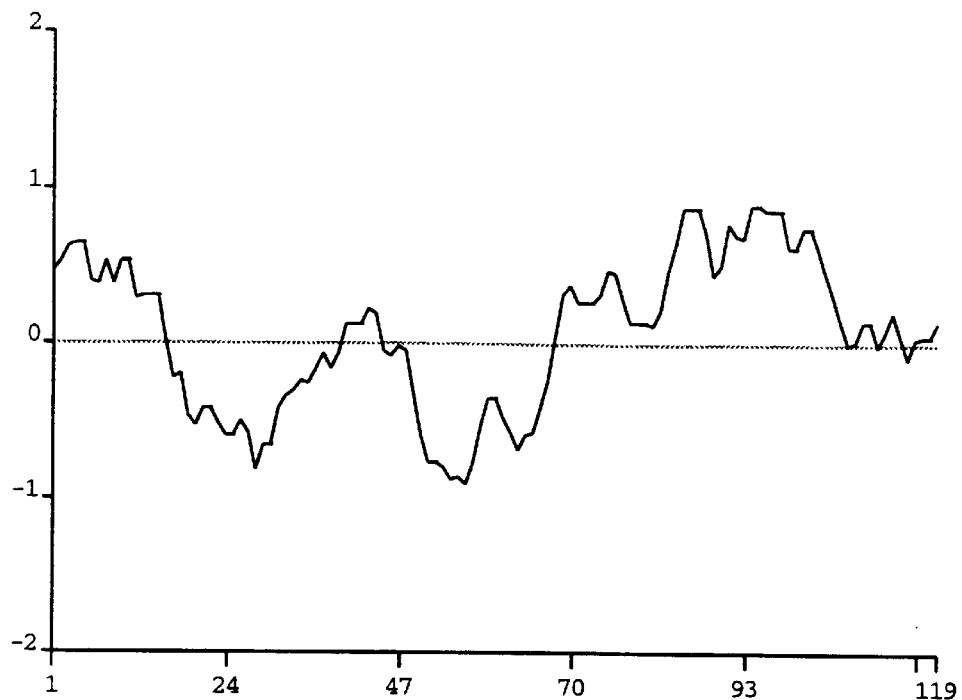
FIGS. 12A and 12B show the hydrophobicity plots for NDS-4, (SEQ ID NO:7) and bovine heart B14.5b subunit, (SEQ ID NO:12).
Figure 12B:
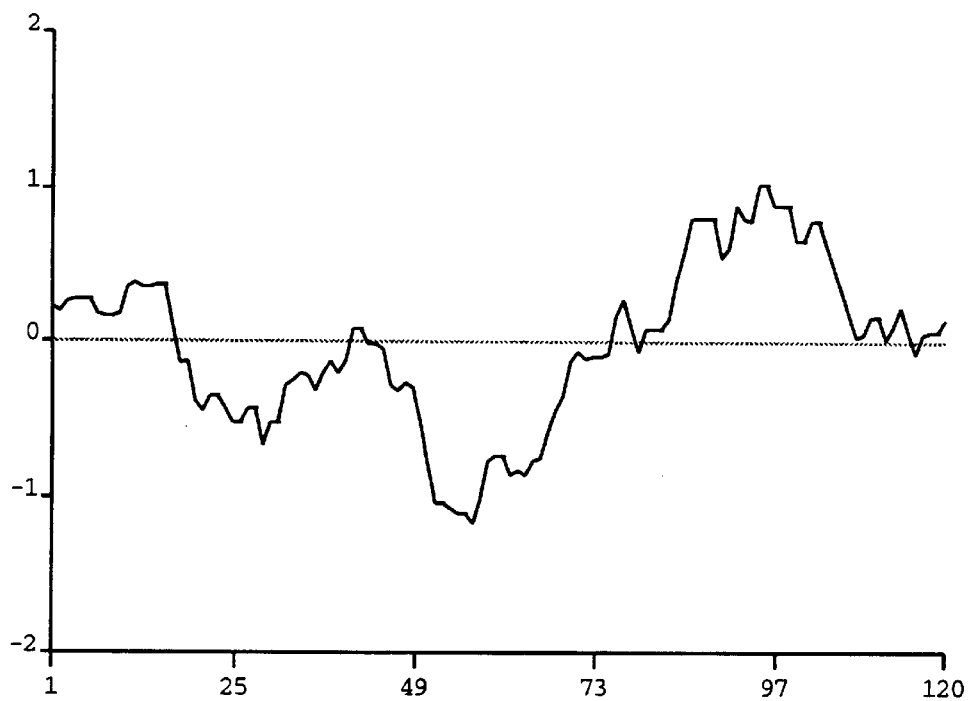

In another embodiment, the invention encompasses a polypeptide comprising the amino acid sequence of SEQ ID NO:7, as shown in FIGS. 4A and 4B NDS-4 is 119 amino acids in length. As shown in FIG. 8, NDS-4 has chemical and structural homology with the bovine 14.5b subunit (GI 582). In particular, NDS-4 and 14.5b share 71% identity. The bovine 14.5b subunit is the only one of the nine nuclear encoded subunits that does not contain an alanine or serine residue adjacent to the initiator methionine and appears to be N-acetylated at the N-terminus without removal of the initiator methionine. NDS-4 shares this feature. As illustrated by FIGS. 12A and 12B, NDS-4 and 14.5b share similar hydrophobicity plots. Neither protein is notably hydrophobic, which is consistent with the occurrence of 14.5b in the extrinsic membrane domain of NADH-D. Northern analysis indicates that partial transcripts of the gene encoding NDS-4 are most abundant in cDNA libraries from cancerous tissues and immortalized cell lines (28/70) and smooth muscle tissues (19/70), with some occurrence in fetal, developing tissues as well.

The invention also encompasses NDS variants. A preferred NDS variant is one having at least 80%, and more preferably 90%, amino acid sequence similarity to the NDS amino acid sequence (SEQ ID NO:1, SEQ ID NO:3, SEQ ID NO:5, or SEQ ID NO:7). A most preferred NDS variant is one having at least 95% amino acid sequence similarity to SEQ ID NO:1, SEQ ID NO:3, SEQ ID NO:5, or SEQ ID NO:7.

The invention also encompasses polynucleotides which encode NDS. Accordingly, any nucleic acid sequence which encodes the amino acid sequence of NDS can be used to generate recombinant molecules which express NDS. In a particular embodiment, the invention encompasses the polynucleotide comprising the nucleic acid of SEQ ID NO:2, SEQ ID NO:4, SEQ ID NO:6, or SEQ ID NO:8 as shown in FIGS. 1A and 1B, 2, and 3.

It will be appreciated by those skilled in the art that as a result of the degeneracy of the genetic code, a multitude of nucleotide sequences encoding NDS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NDS, and all such variations are to be considered as being specifically disclosed.

Although nucleotide sequences which encode NDS and its variants are preferably capable of hybridizing to the nucleotide sequence of the naturally occurring NDS under appropriately selected conditions of stringency, it may be advantageous to produce nucleotide sequences encoding NDS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NDS and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode NDS and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding NDS or any portion thereof Also encompassed by the invention are polynucleotide sequences that are capable of hybridizing to the claimed nucleotide sequences, and in particular, those shown in SEQ ID NO:2, SEQ ID NO:4, SEQ ID NO:6, or SEQ ID NO:8, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–11), and may be used at a defined stringency.

Altered nucleic acid sequences encoding NDS which are encompassed by the invention include deletions, insertions, or substitutions of different nucleotides resulting in a polynucleotide that encodes the same or a functionally equivalent NDS. The encoded protein may also contain deletions, insertions, or substitutions of amino acid residues which produce a silent change and result in a functionally equivalent NDS. Deliberate amino acid substitutions may be made on the basis of similarity in polarity, charge, solubility, hydrophobicity, hydrophilicity, and/or the amphipathic nature of the residues as long as the biological activity of NDS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding NDS. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the Hamilton MICRO-LAB 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding NDS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NDS, or fusion proteins or functional equivalents thereof, may be used in recombinant DNA molecules to direct expression of NDS in appropriate host cells. Due to the inherent degeneracy of the genetic code, other DNA sequences which encode substantially the same or a functionally equivalent amino acid sequence may be produced and these sequences may be used to clone and express NDS.

As will be understood by those of skill in the art, it may be advantageous to produce NDS-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter sequences encoding NDS for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

In another embodiment of the invention, natural, modified, or recombinant polynucleotides encoding NDS may be ligated to a heterologous sequence to encode a fusion protein. For example, to screen peptide libraries for inhibitors of NDS activity, it may be useful to encode a chimeric NDS protein that can be recognized by a commercially available antibody. A fusion protein may also be engineered to contain a cleavage site located between a sequence encoding NDS and the heterologous protein sequence, so that NDS may be cleaved and purified away from the heterologous moiety.

In another embodiment, sequences encoding NDS may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of NDS, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) Proteins, Structures and Molecular Principles, W H Freeman and Co., New York, N.Y.). The composition of the synthetic peptides may be confirmed by amino acid analysis or sequencing (e.g., the Edman degradation procedure; Creighton, supra). Additionally, the amino acid sequence of NDS, or any part thereof, may be altered during direct synthesis and/or combined using chemical methods with sequences from other proteins, or any part thereof, to produce a variant polypeptide.

In order to express a biologically active NDS, the nucleotide sequences encoding NDS or functional equivalents, may be inserted into appropriate expression vectors, i.e., a vector which contains the necessary elements for the transcription and translation of the inserted coding sequence.

Methods which are well known to those skilled in the art may be used to construct expression vectors containing sequences encoding NDS and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding NDS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL), and the like, may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NDS, vectors based on SV40 or EBV may be used with an appropriate selectable marker.

In bacterial systems, a number of expression vectors may be selected depending upon the use intended for NDS. For example, when large quantities of NDS are needed for the induction of antibodies, vectors which direct high level expression of fusion proteins that are readily purified may be used. Such vectors include, but are not limited to, the multifunctional E. coli cloning and expression vectors such as Bluescript® (Stratagene), in which the sequence encoding NDS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding NDS may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express NDS. For example, in one such system, Autographa californica nuclear polyhedrosis virus (AcNPV) is used as a vector to express foreign genes in Spodoptera frugiperda cells or in Trichoplusia larvae. The sequences encoding NDS may be cloned into a non-essential region of the virus, such as the polyhedrin gene, and placed under control of the polyhedrin promoter. Successful insertion of NDS will render the polyhedrin gene inactive and produce recombinant virus lacking coat protein. The recombinant viruses may then be used to infect, for example, *S. frugiperda* cells or Trichoplusia larvae in which NDS may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding NDS may be ligated into an adenovirus transcription/translation complex consisting of the late promoter and tripartite leader sequence. Insertion in a non-essential E1 or E3 region of the viral genome may be used to obtain a viable virus which is capable of expressing NDS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding NDS. Such signals include the ATG initiation codon and adjacent sequences. In cases where sequences encoding NDS, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express NDS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding NDS is inserted within a marker gene sequence, recombinant cells containing sequences encoding NDS can be identified by the absence of marker gene function. Alternatively, a marker gene can be placed in tandem with a sequence encoding NDS under the control of a single promoter. Expression of the marker gene in response to induction or selection usually indicates expression of the tandem gene as well.

Alternatively, host cells which contain sequences encoding and expressing NDS may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of polynucleotide sequences encoding NDS can be detected by DNA-DNA or DNA-RNA hybridization or amplification using probes or portions or fragments of polynucleotides encoding NDS. Nucleic acid amplification based assays involve the use of oligonucleotides or oligomers based on the sequences encoding NDS to detect transformants containing DNA or RNA encoding NDS. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of NDS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NDS is preferred, but a competitive binding assay may be employed. These and other assays are described, among other places, in Hampton, R. et al. (1990; *Serological Methods, Laborato Manual,* APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NDS include oligolabeling, nick translation, end-labeling or PCR amplification using a labeled nucleotide. Alternatively, sequences encoding NDS, or any portion thereof, may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding NDS may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode NDS may be designed to contain signal sequences which direct secretion of NDS through a prokaryotic or eukaryotic cell membrane. Other recombinant constructions may be used to join sequences encoding NDS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and NDS may be used to facilitate purification. One such expression vector provides for expression of a fusion protein containing NDS and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying NDS from the fusion protein. A discussion of vectors which contain fusion proteins is provided in Kroll, D. J. et al. (1993; DNA Cell Biol. 12:441–453).

In addition to recombinant production, fragments of NDS may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizers (Perkin Elmer). Various fragments of NDS may be chemically synthesized separately and combined using chemical methods to produce the full length molecule.

Therapeutics

Based on the chemical and structural homology between NDS-1 and the bovine 30-kDa subunit, and the expression of NDS-1 in cancerous tissues and tissues of the immune system, NDS-1 is believed to play a role in cancer, the development of inflammatory disease and immunological disorders.

Therefore, in one embodiment, a vector expressing antisense of the polynucleotide encoding NDS-1 may be administered to a subject to treat or prevent cancer. Cancers may include, but are not limited to, cancers of the lung, colon, prostate, heart, brain, stomach, intestine, pancreas, breast, ovaries, leukemias and melanomas.

In another embodiment, a vector expressing antisense of the polynucleotide encoding NDS-1 may be administered to a subject to treat or prevent immune system disorders, which may include, but are not limited to conditions such as anemias, asthma, systemic lupus, myasthenia gravis, diabetes mellitus, autoimmune thyroiditis, pancreatitis, ulcerative colitis, osteoporosis, glomerulonephritis; rheumatoid and osteoarthritis; and scleroderma.

In another embodiment, antagonists or inhibitors of NDS-1 may be administered to a subject to treat or prevent cancer, the types of cancer include those described above.

In another embodiment, antagonists or inhibitors of NDS-1 may be administered to a subject to treat or prevent the immune system disorders listed above.

Based on the chemical and structural homology between NDS-2 and the bovine B15 subunit, and the expression of NDS-2 in cancerous tissues and tissues of the sympathetic nervous system (paraganglion and smooth muscle tissues), NDS-2 is believed to play a role in cancers, mitochondrial myopathies, and disorders of the sympathetic nervous system.

Therefore, in one embodiment, NDS-2 or a fragment or derivative thereof may be administered to a subject to treat or prevent mitochondrial myopathies. Such conditions and diseases may include, but are not limited to, progressive external ophthalmoplegia, Kearns-Sayre syndrome, myoclonic epilepsy, encephalopathy, cardiomyopathy, and lactic acidosis.

In another embodiment, a vector capable of expressing NDS-2, or a fragment or a derivative thereof, may also be administered to a subject to treat or prevent the mitochondrial myopathies listed above.

In another embodiment, a vector expressing antisense of the polynucleotide encoding NDS-2 may be administered to a subject to treat or prevent cancer. Cancers may include, but are not limited to, cancers of the heart, ovaries, colon, kidney, bladder, prostate, pancreas, brain, stomach, breast, lung, liver, and leukemias.

In another embodiment, a vector expressing antisense of the polynucleotide encoding NDS-2 may be administered to a subject to treat or prevent disorders of the sympathetic nervous system. Such disorders and diseases may include, but are not limited to, hypertension, cardiovascular shock, arrhythmias, asthma, migraine headaches, and anaphylactic shock.

In another embodiment, antagonists or inhibitors of NDS-2 may be administered to a subject to treat or prevent the types of cancer listed above.

In another embodiment, antagonists or inhibitors of NDS-2 may be administered to a subject to treat or prevent the disorders of the sympathetic nervous system listed above.

Based on the chemical and structural homology between NDS-3 and the bovine 15-kDa (IP) subunit, and the expression of NDS-2 in cancerous tissues, smooth muscle tissues and brain, NDS-3 is believed to play a role in cancer, myopathies, and neurodegenerative diseases.

Therefore, in one embodiment, NDS-3 or a fragment or derivative thereof may be administered to a subject to treat or prevent mitochondrial myopathies. Such conditions and diseases may include, but are not limited to, progressive external ophthalmoplegia, Kearns-Sayre syndrome, myoclonic epilepsy, encephalopathy, cardiomyopathy, and lactic acidosis.

In another embodiment, NDS-3 or a fragment or derivative thereof may be administered to a subject to treat or prevent neurodegenerative diseases. Such diseases and disorders may include, but are not limited to, Alzheimer's disease, Huntington's disease, Parkinson's disease, epilepsy, and Down's syndrome, In another embodiment, a vector capable of expressing NDS-3, or a fragment or a derivative thereof, may also be administered to a subject to treat or prevent myopathies as described above.

In another embodiment, a vector capable of expressing NDS-3, or a fragment or a derivative thereof, may also be administered to a subject to treat or prevent neurodegenerative diseases as described above.

In another embodiment, a vector expressing antisense of the polynucleotide encoding NDS-3 may be administered to a subject to treat or prevent cancers. Cancers may include, but are not limited to, cancers of the ovaries, paraganglion, uterus, kidney, brain, heart, prostate, stomach, bladder, lung, colon, heart, tongue, thyroid, and breast.

In another embodiment, antagonists or inhibitors of NDS-3 may be administered to a subject to treat or prevent cancers as described above.

Based on the chemical and structural homology between NDS-4 (SEQ ID NO:7) and the bovine B14.5b subunit (SEQ ID NO:12), and the expression of NDS-4 in cancerous tissues, and tissues of the sympathetic nervous system (paraganglion and smooth muscle tissues), NDS-4 is believed to play a role in cancer, mitochondrial myopathies, and disorders of the sympathetic nervous system.

Therefore, in one embodiment, NDS-4 or a fragment or derivative thereof may be administered to a subject to treat or prevent mitochondrial myopathies. Such conditions and diseases may include, but are not limited to, progressive external ophthalmoplegia, Kearns-Sayre syndrome, myoclonic epilepsy, encephalopathy, cardiomyopathy, and lactic acidosis.

In another embodiment, a vector capable of expressing NDS-4, or a fragment or a derivative thereof, may also be administered to a subject to treat or prevent myopathies as described above.

In another embodiment, a vector expressing antisense of the polynucleotide encoding NDS-4 may be administered to a subject to treat or prevent cancer. Cancers may include, but are not limited to, cancers of the heart, ovaries, colon, kidney, bladder, prostate, pancreas, brain, stomach, breast, lung, liver, and leukemias.

In another embodiment, a vector expressing antisense of the polynucleotide encoding NDS-4 may be administered to a subject to treat or prevent disorders of the sympathetic nervous system. Such disorders and diseases may include, but are not limited to, hypertension, cardiovascular shock, arrhythmias, asthma, migraine headaches, and anaphylactic shock.

In another embodiment, antagonists or inhibitors of NDS-4 may be administered to a subject to treat or prevent the types of cancer listed above.

In another embodiment, antagonists or inhibitors of NDS-4 may be administered to a subject to treat or prevent the disorders of the sympathetic nervous system listed above.

Antibodies which are specific for NDS may be used directly as an antagonist, or indirectly as a targeting or delivery mechanism for bringing a pharmaceutical agent to cells or tissue which express NDS.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of NDS may be produced using methods which are generally known in the art. In particular, purified NDS may be used to produce antibodies or to screen libraries of pharmaceutical agents to identify those which specifically bind NDS.

Antibodies to NDS may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with NDS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to NDS have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of NDS amino acids may be fused with those of another protein such as keyhole limpet hemocyanin and antibody produced against the chimeric molecule.

Monoclonal antibodies to NDS may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J Immunol. Methods 81:31–42; Cote, R. J. et al. (1983) Proc. Natl. Acad. Sci. 80:2026–2030; Cole, S. P. et al. (1985) Mol Cell Biol. 61:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–55; Neuberger, M. S. et al. (1984) Nature 312:604–8; Takeda, S. et al. (1985) Nature 314:452–4). Alternatively, techniques described for the production of single chain antibodies may be adapted, using methods known in the art, to produce NDS-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–37; Winter, G. et al. (1991) Nature 349:293–9).

Antibody fragments which contain specific binding sites for NDS may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–81).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NDS and its specific antibody. A two-site, monoclonal-based immunoassay utilizing monoclonal antibodies reactive to two non-interfering NDS epitopes is preferred, but a competitive binding assay may also be employed (Maddox, supra).

In another embodiment of the invention, the polynucleotides encoding NDS, or any fragment thereof, or antisense molecules, may be used for therapeutic purposes. In one aspect, antisense to the polynucleotide encoding NDS may be used in situations in which it would be desirable to block the transcription of mRNA. In particular, cells may be transformed with sequences complementary to polynucleotides encoding NDS. Thus, antisense sequences may be used to modulate NDS activity, or to achieve regulation of gene function. Such technology is now well known in the art, and sense or antisense oligomers or larger fragments, can be designed from various locations along the coding or control regions of sequences encoding NDS.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding NDS. These techniques are described both in Sambrook et al. (supra) and in Ausubel et al. (supra).

Genes encoding native NDS can be turned off by transforming a cell or tissue with expression vectors which express high levels of the polynucleotide, or fragment thereof, which encodes NDS. Such constructs may be used to introduce untranslatable sense or antisense sequences into a cell. Even in the absence of integration into the genomic DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding NDS, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NDS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NDS. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NDS, antibodies to NDS, mimetics, agonists, antagonists, or inhibitors of NDS. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NDS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NDS or fragments thereof, antibodies of NDS, agonists, antagonists or inhibitors of NDS, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind NDS may be used for the diagnosis of conditions or diseases characterized by expression of NDS, or in assays to monitor patients being treated with NDS, agonists, antagonists or inhibitors. The antibodies useful for diagnostic purposes may be prepared in the same manner as those described above for therapeutics. Diagnostic assays for NDS include methods which utilize the antibody and a label to detect NDS in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NDS are known in the art and provide a basis for diagnosing altered or abnormal levels of NDS expression. Normal or standard values for NDS expression are established by combining body fluids or cell extracts taken from normal mammalian subjects, preferably human, with antibody to NDS under conditions suitable for complex formation The amount of standard complex formation may be quantified by various methods, but preferably by photometric, means. Quantities of NDS expressed in subject samples, control and disease, from biopsied tissues are compared with the standard values. Deviation between standard and subject values establishes the parameters for diagnosing disease.

In another embodiment of the invention, the polynucleotides encoding NDS may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of NDS may be correlated with disease. The diagnostic assay may be used to distinguish between absence, presence, and excess expression of NDS, and to monitor regulation of NDS levels during therapeutic intervention.

In one aspect, hybridization with PCR probes which are capable of detecting polynucleotide sequences, including genomic sequences, encoding NDS or closely related molecules, may be used to identify nucleic acid sequences which encode NDS. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NDS, alleles, or related sequences.

Probes may also be used for the detection of related sequences, and should preferably contain at least 50% of the nucleotides from any of the sequences encoding NDS. The hybridization probes of the subject invention may be DNA or RNA and derived from the nucleotide sequences of SEQ ID NO:2, SEQ ID NO:4, SEQ ID NO:6 or SEQ ID NO:8 or from genomic sequence including promoter, enhancer elements, and introns of the naturally occurring NDS.

Means for producing specific hybridization probes for DNAs encoding NDS include the cloning of nucleic acid sequences encoding NDS or NDS derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding NDS may be used for the diagnosis of conditions or diseases which are associated with expression of NDS. Examples of such conditions or diseases include cancers of the heart, breast, colon, and prostate, neurodegenerative diseases such as Alzheimer's and Huntington's disease, immunological disorders such as anemias, asthma, systemic lupus, myasthenia gravis, diabetes mellitus, autoimmune thyroiditis, pancreatitis, ulcerative colitis, osteoporosis, glomerulonephritis; rheumatoid and osteoarthritis; and scleroderma, myopathies such as progressive external ophthalmoplegia, Kearns-Sayre syndrome, myoclonic epilepsy, encephalopathy, cardiomyopathy, and lactic acidosis, and disorders of the sympathetic nervous system such as hypertension, cardiovascular shock, arrhythmias, asthma, migraine headaches, and anaphylactic shock. The polynucleotide sequences encoding NDS may be used in Southern or northern analysis, dot blot, or other membrane-based technologies; in PCR technologies; or in dip stick, pin, ELISA or chip assays utilizing fluids or tissues from patient biopsies to detect altered NDS expression. Such qualitative or quantitative methods are well known in the art.

In a particular aspect, the nucleotide sequences encoding NDS may be useful in assays that detect activation or induction of various cancers, particularly those mentioned above. The nucleotide sequences encoding NDS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NDS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NDS, a normal or standard profile for expression is established. This may be accomplished by combining body fluids or cell extracts taken from normal subjects, either animal or human, with a sequence, or a fragment thereof, which encodes NDS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NDS may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NDS include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes NDS may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma, R. S. et al. (1988) *Human Chromosomes: A Manual Of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding NDS on a physical chromosomal map and a specific disease, or predisposition to a specific disease, may help delimit the region of DNA associated with that genetic disease. The nucleotide sequences of the subject invention may be used to detect s differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NDS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NDS and the agent being tested, may be measured.

Another technique for drug screening which may be used provides for high throughput screening of compounds having suitable binding affinity to the protein of interest as described in published PCT application WO84/03564. In this method, as applied to NDS, large numbers of different small test compounds are synthesized on a solid substrate, such as plastic pins or some other surface. The test compounds are reacted with NDS, or fragments thereof, and washed. Bound NDS is then detected by methods well known in the art. Purified NDS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NDS specifically compete with a test compound for binding NDS. In this manner, the antibodies can be used to detect the presence of any peptide which shares one or more antigenic determinants with NDS.

In additional embodiments, the nucleotide sequences which encode NDS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction
HMC1NOT01

The human mast cell HMC1NOT01 cDNA library was constructed by Stratagene (Stratagene, La Jolla Calif.) using mRNA purified from cultured HMC-1 cells. The library was prepared by Stratagene essentially as described. The human mast cell HMC1NOT01 cDNA library was prepared by purifying poly(A+)RNA (mRNA) from human mast cells and then enzymatically synthesizing double stranded complementary DNA (cDNA) copies of the mRNA. Synthetic adaptor oligonucleotides were ligated onto the ends of the cDNA enabling its insertion into the lambda vector. The HMC1NOT01 library was constructed using the UINZAP vector system (Stratagene), allowing high efficiency unidirectional (sense orientation) lambda library construction and the convenience of a plasmid system with blue/white color selection to detect clones with cDNA insertions.

BLADNOT03

The BLADNOT03 cDNA library was constructed from microscopically normal bladder tissue obtained from a 80-year-old Caucasian female. The normal tissue from the anterior wall was excised along with the tumorous tissue during a radical cysterectomy of a grade 3 of 4 invasive transitional cell carcinoma located on the posterior wall. Prior to surgery the patient had a history of a malignant neoplasm of the uterus, a total hysterectomy, removal of the fallopian tubes and ovaries, partial thyroidectomy, aortocoronary bypass, hypertension, and atherosclerosis. The patient was receiving the following medications: COUMADIN (DuPont Pharmaceuticals, Wilmington, Pa.), KLOTRIX (Bristol Laboratories, Evansville, Ind.), LASIX (Hoechst-Roussel Pharmaceuticals, Inc., Somerville, N.J.), digoxin, and atenolol. There was a family history of atherosclerosis in the father and a sibling, and osteoarthritis in the mother.

The frozen tissue was homogenized and lysed using a Brinkmann Polyron PT-3000 homogenizer (Brinkmann Instruments, Westbury, N.J.) in guanidinium isothiocyanate solution. The lysate was centrifuged over a 5.7 M CsCl cushion using a Beckman SW28 rotor in a Beckman L8-70M ULTRACENTRIFUGE (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen OLIGOTEX kit (QIAGEN, Inc.; Chatsworth, Calif.) and used to construct the cDNA library.

The mRNA was handled according to the recommended protocols in the SUPERSCRIPT plasmid system for cDNA synthesis and plasmid cloning (Cat. #18248-013, Gibco BRL). A new plasmid was constructed using the following procedures: The commercial plasmid pSPORT 1 (Gibco BRL) was digested with Eco RI restriction enzyme (New England Biolabs, Beverley, Mass.), the overhanging ends of the plasmid were filled with Klenow enzyme (New England Biolabs) and 2'-deoxynucleotide-5'-triphosphates (dNTPs), and the intermediate plasmid was self-ligated and transformed into the bacterial host, E. coli strain JM109.

Quantities of this intermediate plasmid were digested with Hind III restriction enzyme (New England Biolabs), the overhanging ends were filled with Klenow and dNTPs, and a 10-mer linker of sequence 5' . . . CGGAATTCCG . . . 3' was phosphorylated and ligated onto the blunt ends. The product of the ligation reaction was digested with EcoRI and self-ligated. Following transformation into JM109 host cells, plasmids designated pINCY were isolated and tested for the ability to incorporate cDNAs using Not I and Eco RI restriction enzymes.

BLADNOT03 cDNAs were fractionated on a SEPHAROSE CL4B column (Cat. #275105-01, Pharmacia), and those cDNAs exceeding 400 bp were ligated into pINCY I. The plasmid pINCY I was subsequently transformed into DH5α competent cells (Cat. #18258-012, Gibco BRL).

PROSNOT16

The PROSNOT16 cDNA library was constructed from microscopically normal prostate obtained from a 68-year-old Caucasian male. The normal prostate tissue was excised during a radical prostatectomy along with prostate tissue for which the pathology report indicated was associated with a Gleason grade 3+4 adenocarcinoma which perforated the capsule to involve periprostatic tissue. Surgical margins (distal urethra, right and left bladder bases, right and left apices) were negative for tumor. Initially, the patient presented with elevated prostate specific antigen (PSA) after which he was diagnosed with a malignant neoplasm of the prostate and myasthenia gravis. The patient history included benign hypertension, cerebrovascular disease, arteriosclerotic coronary artery disease, osteoarthritis, type II diabetes without complications, acute myocardial infarction, and alcohol use. The patient's family history included benign hypertension, an episode of acute myocardial infarction, and hyperlipidemia in the patient's mother, and arteriosclerotic coronary artery disease and an episode of acute myocardial infarction in the patient's sibling. The patient was taking PREDNISONE (The Upjohn Company, Kalamazoo, Mich.) and DIABETA (glyburide; Hoechst-Roussel Pharmaceuticals Inc., Somerville, N.J.).

The frozen tissue was homogenized and lysed using a Brinkmann Polytron PT-3000 Homogenizer (Brinkmann Instruments, Westbury, N.J.) in guanidinium isothiocyanate solution. The lysates were centrifuged over a 5.7 M CsCl cushion using a Beckman SW28 rotor in a Beckman L8-70M ULTRACENTRIFUGE (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen OLIGOTEX kit (QIAGEN, Inc., Chatsworth, Calif.) and used to construct the cDNA libraries.

The mRNA was handled according to the recommended protocols in the SUPERSCRIPT plasmid system for cDNA synthesis and plasmid cloning (Cat. #18248-013, Gibco BRL). A new plasmid was constructed using the following procedures: The commercial plasmid pSPORT 1 (Gibco BRL) was digested with Eco RI restriction enzyme (New England Biolabs, Beverley, Mass.), the overhanging ends of the plasmid were filled with Klenow enzyme (New England Biolabs) and 2'-deoxynucleotide-5'-triphosphates (dNTPs) ,and the intermediate plasmid was self-ligated and transformed into the bacterial host, E. coli strain JM109.

Quantities of this intermediate plasmid were digested with Hind III restriction enzyme (New England Biolabs), the overhanging ends were filled with Klenow and dNTPs, and a 10-mer linker of sequence 5' . . . CGGAATTCCG . . . 3' was phosphorylated and ligated onto the blunt ends. The product of the ligation reaction was digested with EcoRI and self-ligated. Following transformation into JM109 host cells, plasmids designated pINCY were isolated and tested for the ability to incorporate cDNAs using Not I and Eco RI restriction enzymes.

BLADNOT03 cDNAs were fractionated on a SEPHAROSE CL4B column (Cat. #275105-01, Pharmacia), and those cDNAs exceeding 400 bp were ligated into pINCY I. The plasmid pINCY I was subsequently transformed into DH5α competent cells (Cat. #18258-012, Gibco BRL).

BRSTTUT03

The BRSTTUT03 cDNA library was constructed from cancerous breast tissue removed from a 58-year-old Caucasian female who had undergone unilateral extended simple mastectomy following diagnosis of multicentric invasive grade 4 mammary lobular carcinoma. The pathology report indicated that tumor cells were identified in the upper outer quadrant of the left breast, forming a single predominant mass. Tumor cells were also identified in the lower outer quadrant of the left breast, forming three separate nodules. The surgical margins were found negative for tumor. The skin, nipple, and fascia were uninvolved. No evidence of vascular invasion was found. Eight mid low and two high left axillary lymph nodes were found negative for tumor. Prior to surgery, the patient was prescribed tamoxifen to inhibit the induction of mammary carcinoma. The patient was also taking ZANTAC (ranitidine hydrochloride; Glaxo Wellcome, Inc., Research Triangle Park, N.C.), aspirin, extra-strength TYLENOL (acetaminophen; McNeil Consumer Products Company, Fort Washington, Pa. ), and vitamin C. Prior to surgery, the patient was diagnosed with skin cancer, cerebrovascular disease, atherosclerosis, rheumatic heart disease, and osteoarthritis. The patient family history included breast cancer in patient's mother and prostate cancer in patient's brother. This library is an extension of the cDNA library BRSTTUT03.

The frozen tissue was homogenized and lysed using a Brinkmann Polytron PT-3000 homogenizer (Brinkmann Instruments, Westbury, N.J.) in guanidinium isothiocyanate solution. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen OLIGOTEX kit (QIAGEN, Inc.; Chatsworth, Calif.) and used to construct the cDNA library.

The mRNA was handled according to the recommended protocols in the SUPERSCRIPT plasmid system for cDNA synthesis and plasmid cloning (Cat. #18248-013; Gibco/BRL). cDNAs were fractionated on a SEPHAROSE CL4B column (Cat. #275105-01; Pharmacia), and those cDNAs exceeding 400 bp were ligated into pSport I. The plasmid pSport I was subsequently transformed into DH12S competent cells (Cat. #18312-017; Gibco/BRL).

II Isolation and Sequencing of cDNA Clones

Plasmid DNA was released from the cells and purified using the R.E.A.L. PREP96 plasmid kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIEST™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

Alternative methods of purifying plasmid DNA include the use of MAGIC MINIPREPS DNA purification system (Cat. No. A7100, Promega) or QIAWELL-8 Plasmid, QIAWELL PLUS and QIAWELL ULTRA DNA purification systems (Qiagen, Inc.).

The cDNAs were sequenced by the method of Sanger F. and A. R. Coulson (1975; J. Mol. Biol. 94:441f), using a Hamilton MICROLAB 2200 (Hamilton, Reno Nev.) in combination with four Peltier Thermal Cyclers (PTC200 from MJ Research, Watertown Mass.) and Applied Biosystems 377 or 373 DNA sequencing systems (Perkin Elmer) and reading frame was determined.

III Homology Searching of cDNA Clones and their Deduced Proteins

Each cDNA was compared to sequences in GenBank using a search algorithm developed by Applied Biosystems and incorporated into the INHERIT-670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul, S. F. et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals, Inc.). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score 100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding NDS occurs. Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding NDS to Full Length or to Recover Regulatory Sequences Polynucleotides encoding NDS (SEQ ID NO:2, SEQ ID NO:4, SEQ ID NO:6, or SEQ ID NO:8) are used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| Step | Condition |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step | Condition |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2, SEQ ID NO:4, SEQ ID NO:6, or SEQ ID NO:8 are employed to screen cDNAs, genomic DNAs, or mRNAs. Although the labeling of oligonucleotides, consisting of about 20 basepairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots or the blots are exposed in a Phosphoimager cassette (Molecular Dynamics, Sunnyvale, Calif.) hybridization patterns are compared visually.

VII Antisense Molecules

Antisense molecules to the NDS-encoding sequence, or any part thereof, is used to inhibit in vivo or in vitro expression of naturally occurring NDS. Although use of antisense oligonucleotides, comprising about 20 base-pairs, is specifically described, essentially the same procedure is used with larger cDNA fragments. An oligonucleotide based on the coding sequences of NDS, as shown in FIGS. 1A, 1B, 1C, 2A, 2B, 3A, 3B, 4A, and 4B are used to inhibit expression of naturally occurring NDS. The complementary oligonucleotide is designed from the most unique 5' sequence as shown in FIGS. 1A, 1B, and 1C and used either to inhibit transcription by preventing promoter binding to the upstream nontranslated sequence or translation of an NDS-encoding transcript by preventing the ribosome from binding. Using an appropriate portion of the signal and 5' sequence of SEQ ID NO:2, SEQ ID NO:4, SEQ ID NO:6, or SEQ ID NO:8, an effective antisense oligonucleotide includes any 15–20 nucleotides spanning the region which translates into the signal or 5' coding sequence of the polypeptide as shown in FIGS. 1A, 1B, 1C, 2A, 2B, 3A, 3B, 4A, and 4B.

VIII Expression of NDS

Expression of NDS is accomplished by subcloning the cDNAs into appropriate vectors and transforming the vectors into host cells. In this case, the cloning vector, pSport, previously used for the generation of the cDNA library is used to express NDS in *E. coli*. Upstream of the cloning site, this vector contains a promoter for B-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of NDS into the bacterial growth media which can be used directly in the following assay for activity.

IX Demonstration of NDS Activity

NDS activity is measured in the reconsituted NADH-D complex by the catalysis of electron transfer from NADH to decylubiquinone (DB). The reaction contains 10 ug/mL NADH-D protein, 2 uM NADH in 50 mM tris-HCL buffer, pH 7.5, 50 mM NaCl, and 1 mM KCN. The reaction is started by addition of DB at 2 uM and followed by the change in absorbance at 340 nm due to the oxidation of NADH using an ultraviolet spectrophotometer. The activity of NDS is proportional to the rate of change of absorbance at 340 nm.

X Production of NDS Specific Antibodies

NDS that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, SEQ ID NO:6, or SEQ ID NO:8 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 413A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NDS Using Specific Antibodies

Naturally occurring or recombinant NDS is substantially purified by immunoaffinity chromatography using antibodies specific for NDS. An immunoaffinity column is constructed by covalently coupling NDS antibody to an activated chromatographic resin, such as CnBr-activated SEPHAROSE (Pharmacia & Upjohn). After the coupling, the resin is blocked and washed according to the manufacturer's instructions.

Media containing NDS is passed over the immunoaffinity column, and the column is washed under conditions that allow the preferential absorbance of NDS (e.g., high ionic strength buffers in the presence of detergent). The column is eluted under conditions that disrupt antibody/NDS binding (eg, a buffer of pH 2–3 or a high concentration of a chaotrope, such as urea or thiocyanate ion), and NDS is collected.

XII Identification of Molecules which Interact with NDS

NDS or biologically active fragments thereof are labeled with $^{125}$I Bolton-Hunter reagent (Bolton, A. E. and W. M. Hunter (1973) Biochem. J. 133: 529–39). Candidate molecules previously arrayed in the wells of a multi-well plate are incubated with the labeled NDS, washed and any wells with labeled NDS complex are assayed. Data obtained using different concentrations of NDS are used to calculate values for the number, affinity, and association of NDS with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polypeptide selected from the group consisting of:
    a) a recombinant human polypeptide comprising the amino acid sequence of SEQ ID NO:1, said recombinant polypeptide being free of other human amino acid sequences, and
    b) a recombinant polypeptide comprising a naturally occurring human amino acid sequence at least 90% identical to the amino acid sequence of SEQ ID NO:1, said recombinant polypeptide being free of other human amino acid sequences.

2. An isolated polypeptide of claim 1, comprising the amino acid sequence of SEQ ID NO:1.

3. An isolated polypeptide of claim 1, comprising a naturally occurring human amino acid sequence at least 90% identical to the amino acid sequence of SEQ ID NO:1, said polypeptide being free of other human amino acid sequences.

4. An isolated polypeptide of claim 1, comprising a naturally occurring human amino acid sequence at least 95% identical to the amino acid sequence of SEQ ID NO:1, said polypeptide being free of other human amino acid sequences.

5. A composition comprising a polypeptide of claim 1 and a pharmaceutically acceptable excipient.

6. A composition comprising a polypeptide of claim 2 and a pharmaceutically acceptable excipient.

7. A composition comprising a polypeptide of claim 3 and a pharmaceutically acceptable excipient.

8. A composition comprising a polypeptide of claim 4 and a pharmaceutically acceptable excipient.

9. A method for producing a polypeptide of claim 1, the method comprising:
    a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1, and b) recovering the polypeptide so expressed.

10. A method for screening a compound for effectiveness as an agonist of a polypeptide of claim 1, the method comprising:

a) exposing a sample comprising a polypeptide of claim 1 to a compound, and b) detecting agonist activity in the sample.

11. A method for screening a compound for effectiveness as an antagonist of a polypeptide of claim 1, the method comprising:

a) exposing a sample comprising a polypeptide of claim 1 to a compound, and b) detecting antagonist activity in the sample.

12. A method of screening for a compound that specifically binds to the polypeptide of claim 1, said method comprising the steps of:

a) combining the polypeptide of claim 1 with at least one test compound under suitable conditions, and b) detecting binding of the polypeptide of claim 1 to the test compound, thereby identifying a compound that specifically binds to the polypeptide of claim 1.

13. A method of screening for a compound that modulates the activity of the polypeptide of claim 1, said method comprising:

a) combining the polypeptide of claim 1 with at least one test compound under conditions permissive for the activity of the polypeptide of claim 1, b) assessing the activity of the polypeptide of claim 1 in the presence of the test compound, and c) comparing the activity of the polypeptide of claim 1 in the presence of the test compound with the activity of the polypeptide of claim 1 in the absence of the test compound, wherein a change in the activity of the polypeptide of claim 1 in the presence of the test compound is indicative of a compound that modulates the activity of the polypeptide of claim 1.

* * * * *